(12) United States Patent
Schwichtenberg et al.

(10) Patent No.: US 7,000,330 B2
(45) Date of Patent: Feb. 21, 2006

(54) METHOD AND APPARATUS FOR RECEIVING A REMOVABLE MEDIA MEMBER

(75) Inventors: Jay Schwichtenberg, New Hope, MN (US); Aravind Padmanabhan, Plymouth, MN (US); Robert Demers, Elk River, MN (US)

(73) Assignee: Honeywell International Inc., Morristown, NJ (US)

( * ) Notice: Subject to any disclaimer, the term of this patent is extended or adjusted under 35 U.S.C. 154(b) by 83 days.

(21) Appl. No.: 10/612,664

(22) Filed: Jul. 2, 2003

(65) Prior Publication Data

US 2004/0211077 A1 Oct. 28, 2004

Related U.S. Application Data

(60) Provisional application No. 60/404,876, filed on Aug. 21, 2002.

(51) Int. Cl.
*G01B 5/25* (2006.01)

(52) U.S. Cl. .......................... 33/645; 33/613
(58) Field of Classification Search ................. 33/613, 33/623, 645, 655; 360/96.5; 385/52; 439/246, 439/526
See application file for complete search history.

(56) References Cited

U.S. PATENT DOCUMENTS

| | | |
|---|---|---|
| 2,403,692 A | 7/1946 | Tibbetts |
| 2,975,307 A | 3/1961 | Shroeder et al. |
| 3,304,446 A | 2/1967 | Martinek et al. |
| 3,381,623 A | 5/1968 | Elliot |
| 3,414,010 A | 12/1968 | Sparrow |

(Continued)

FOREIGN PATENT DOCUMENTS

| | | |
|---|---|---|
| DE | 19617852 | 1/1993 |
| EP | 0744821 A2 | 11/1996 |
| EP | 0744821 A3 | 12/1996 |
| EP | 1001326 | 5/1999 |
| JP | 05-219760 | 8/1993 |
| JP | 02-86258 | 10/1995 |
| SU | 744877 | 6/1980 |
| WO | WO 95/27199 | 3/1995 |
| WO | WO 99/60397 | 4/1999 |
| WO | WO 01/09598 | 7/2000 |
| WO | 02/10713 A | 2/2002 |

OTHER PUBLICATIONS

"Applying Microfluidic Chemical Analytical Systems To Imperfect Samples", P. Yager et al., Micro Total Analysis Systems 98, D. Harrison & A. van den Berg (ed.), Kluwer Academic Publishers, Dordrecht, 207–212, 1998.
"Design Of Microfluidic Sample Preconditioning Systems For Detection Of Biological Agents In Environmental Samples", Yager, M. et al., SPIE Proceedings, 3515, 252–259, 1998.
"Development Of A Flow Cytometry Based Miniature Chemical Fluid Analysis System Using Fluorescent Microbeads", M. Huang. et al., SPIE Biomedical Optics, BIOS 97, conference proceedings, 1997.
"Differential Blood Cell Counts Obtained Using A Microchannel Based Flow Cytometer", E. Altendorf et al., Solid State Sensors & Actuators, vol. 1, 531, 1997.

(Continued)

*Primary Examiner*—G. Bradley Bennett
(74) *Attorney, Agent, or Firm*—Kris T. Fredrick

(57) ABSTRACT

The present invention is directed towards receiving removable media, and in some embodiments, providing tighter alignment tolerances between an inserted removable media member and a receiving device. The present invention is also directed towards providing one or more electrical or optical device on or in the removable media member itself, and for providing an electrical and/or optical link between the one or more electrical and/or optical devices on or in the removable media and the receiving device.

71 Claims, 11 Drawing Sheets

U.S. PATENT DOCUMENTS

| | | |
|---|---|---|
| 3,641,373 A | 2/1972 | Elkuch |
| 3,726,296 A | 4/1973 | Freidland et al. |
| 3,769,531 A | 10/1973 | Elkuch |
| 3,803,424 A | 4/1974 | Smiley et al. |
| 3,827,457 A | 8/1974 | Vutz et al. |
| 3,877,075 A | 4/1975 | Watanabe |
| 3,947,644 A | 3/1976 | Uchikawa |
| 3,976,862 A | 8/1976 | Curbelo |
| 4,115,036 A | 9/1978 | Paterson |
| 4,140,936 A | 2/1979 | Bullock |
| 4,197,737 A | 4/1980 | Pittman |
| 4,244,109 A * | 1/1981 | Silverman .................... 33/645 |
| 4,418,886 A | 12/1983 | Holzer |
| 4,453,169 A | 6/1984 | Martner |
| 4,478,076 A | 10/1984 | Bohrer |
| 4,478,077 A | 10/1984 | Bohrer |
| 4,498,112 A | 2/1985 | Georgens et al. |
| 4,498,850 A | 2/1985 | Perlov et al. |
| 4,501,144 A | 2/1985 | Higashi et al. |
| 4,539,575 A | 9/1985 | Nilsson |
| 4,539,614 A | 9/1985 | Thompson |
| 4,576,050 A | 3/1986 | Lambert |
| 4,651,564 A | 3/1987 | Johnson et al. |
| 4,654,546 A | 3/1987 | Kirjavainen |
| 4,673,995 A | 6/1987 | Spiegelstein |
| 4,683,159 A | 7/1987 | Bohrer et al. |
| 4,721,365 A * | 1/1988 | Nishimura ................... 33/613 |
| 4,722,360 A | 2/1988 | Odajima et al. |
| 4,745,279 A | 5/1988 | Karkar et al. |
| 4,756,508 A | 7/1988 | Giachino et al. |
| 4,821,999 A | 4/1989 | Ohtaka |
| 4,874,949 A | 10/1989 | Harris et al. |
| 4,898,200 A | 2/1990 | Odajima et al. |
| 4,911,616 A | 3/1990 | Laumann, Jr. |
| 4,938,742 A | 7/1990 | Smits |
| 4,939,405 A | 7/1990 | Okuyama et al. |
| 5,065,978 A | 11/1991 | Albarda et al. |
| 5,069,419 A | 12/1991 | Jerman |
| 5,078,581 A | 1/1992 | Blum et al. |
| 5,085,562 A | 2/1992 | van Lintel |
| 5,096,388 A | 3/1992 | Weinberg |
| 5,129,794 A | 7/1992 | Beatty |
| 5,148,074 A | 9/1992 | Fujita et al. |
| 5,171,132 A | 12/1992 | Miyazaki et al. |
| 5,176,358 A | 1/1993 | Bonne et al. |
| 5,180,288 A | 1/1993 | Richter et al. |
| 5,185,641 A | 2/1993 | Igushi et al. |
| 5,192,197 A | 3/1993 | Culp |
| 5,206,557 A | 4/1993 | Bobbio |
| 5,219,278 A | 6/1993 | van Lintel |
| 5,224,843 A | 7/1993 | van Lintel |
| 5,368,704 A | 11/1994 | Madou et al. |
| 5,441,597 A | 8/1995 | Bonne et al. |
| 5,452,878 A | 9/1995 | Gravesen et al. |
| 5,499,909 A | 3/1996 | Yamada et al. |
| 5,528,045 A | 6/1996 | Hoffman et al. |
| 5,537,376 A | 7/1996 | Iluma |
| 5,541,465 A | 7/1996 | Higuchi et al. |
| 5,552,654 A | 9/1996 | Konno et al. |
| 5,571,401 A | 11/1996 | Lewis et al. |
| 5,601,080 A | 2/1997 | Oppenheimer |
| 5,633,724 A | 5/1997 | King et al. |
| 5,642,015 A | 6/1997 | Whitehead et al. |
| 5,683,159 A | 11/1997 | Johnson |
| 5,716,852 A | 2/1998 | Yager et al. |
| 5,725,363 A | 3/1998 | Bustgens et al. |
| 5,726,751 A | 3/1998 | Altendorf et al. |
| 5,757,476 A | 5/1998 | Nakomoto et al. |
| 5,759,014 A | 6/1998 | Van Lintel |
| 5,759,015 A | 6/1998 | Van Lintel et al. |
| 5,793,485 A | 8/1998 | Gourley |
| 5,799,030 A | 8/1998 | Brenner |
| 5,822,170 A | 10/1998 | Cabuz et al. |
| 5,836,750 A | 11/1998 | Cabuz |
| 5,863,502 A | 1/1999 | Southgate et al. |
| 5,863,708 A | 1/1999 | Zanzucchi et al. |
| 5,880,474 A | 3/1999 | Norton et al. |
| 5,893,722 A | 4/1999 | Hibbs-Brenner et al. |
| 5,897,097 A | 4/1999 | Biegelsen et al. |
| 5,901,939 A | 5/1999 | Cabuz et al. |
| 5,911,872 A | 6/1999 | Lewis et al. |
| 5,922,210 A | 7/1999 | Brody et al. |
| 5,932,100 A | 8/1999 | Yager et al. |
| 5,948,684 A | 9/1999 | Weigl et al. |
| 5,971,158 A | 10/1999 | Yager et al. |
| 5,972,710 A | 10/1999 | Weigl et al. |
| 5,974,867 A | 11/1999 | Forster et al. |
| 6,007,775 A | 12/1999 | Yager |
| 6,014,358 A | 1/2000 | Kabasawa |
| 6,082,185 A | 7/2000 | Saaski |
| 6,097,485 A | 8/2000 | Lievan |
| 6,106,245 A | 8/2000 | Cabuz |
| 6,139,800 A | 10/2000 | Chandler |
| 6,179,586 B1 | 1/2001 | Herb et al. |
| 6,184,607 B1 | 2/2001 | Cabuz et al. |
| 6,215,221 B1 | 4/2001 | Cabuz et al. |
| 6,249,341 B1 | 6/2001 | Basiji et al. |
| 6,288,472 B1 | 9/2001 | Cabuz et al. |
| 2001/0012707 A1 * | 8/2001 | Ho et al. .................... 439/526 |
| 2002/0020773 A1 | 2/2002 | Hiroshi et al. |
| 2004/0175986 A1 * | 9/2004 | Liao et al. .................. 439/526 |

OTHER PUBLICATIONS

"Diffusion–Based Optical Chemical Detection In Silicon Flow Structures", B. Weigl et al., Analytical Methods & Instrumentation, μTTAS 96 special edition, 1996.

"Fluorescence And Absorbance Analyte Sensing In Whole Blood And Plasma Based On Diffusion Separation In Silicon–Microfabricated Flow Structures (T–Sensors ™)", B. Weigl, et al., Biomedical Optics, vol. 6, No. 1, Jul. 1997.

"Implementation Of Novel Optical Detection Methods For Clinically Important Blood Analytes Using Microfabricated Flow Structures (T–Sensors™)", E. Altendorf & B. Weigl, MicroTAS 98, Banff, Canada, Apr. 1998.

"Integration Of Microelectrodes With Etched Microchannels For In–Stream Electrochemical Analysis", R.Darling et al., MicroTAS 98, Banff, Canada, Apr. 1998.

"Microfabrication Technology For Research And Diagnostics, Silicon Microchannel Optical Flow Cytometry", E. Altendorf et al., SPIE Proceedings, Biomedical Optics 96, Jan. 1996.

"Microfluidic Approaches To Immunoassays", A. Hatch et al., SPIE conference on Micromachining and Microfabrication Symposium at Santa Clara, CA, Sep. 20–22, 1999.

"Microfluidic Diffusion Based Electrochemical Detection Using Microfabricated Flow Structures (T–Sensors™)", B. Weigl, Analytical Chemistry, submitted 1999.

"Microfluidic Diffusion–Based Separation And Detection", B. Weigl & P. Yager, Science, vol. 283, pp 346–7, Jan. 15, 1999.

"Optical And Electrochemical Diffusion–Based Detection Of Analytes In Complex Samples Using Microfabricated Flow Structures (T–SensorSTM)", B. Weigl, R. Darling, P. Yager, J. Kriebel & K. Mayes, Micro– and nanofabn'cated electro–optical mechanical systems for biomedical and environmental applications II– SPIE vol. 3606, Jan. 25–26, 1999.

"Rapid Sequential Chemical Analysis Using Multiple Fluorescent Reporter Beads", B. Weigl et al., µTTAS 96 Conference Proceedings, 1996.

"Results Obtained Using A Prototype Microfluidics–Based Hematology Analyzer", E.Altendorf et al., SPIE Biomedical Optics 97, 1997.

"Silicon–Microfabricated Diffusion–Based Optical Chemical Sensor", B. Weigh & P. Yager, Reprint from "Sensors & Actuators" B 38–39, 452–457, 1997.

"Simultaneous Self–Referencing Analyte Determination In Complex Sample Solutions Using Microfabricated Flow Structures (T–Sensors™)", B. Weigl et al., Proceedings of MicroTAS 98, 81–4, Banff, Canada, 1998.

"Whole Blood Assays Using Microfluidics–Based T–SensorSTm Technology", B. Weigl, Medical Design Online, http://news.medicaldesignonline.com/featuresarticles/19990416–5922.html, Apr. 1999.

"Large–Scale Linearization Circuit For Electrostatic Motors" IBM Technical Disclosure Bulletin, US. IBM Corp. New York, vol. 37, No. 10, Oct. 1, 1994, pp. 563–564, XP000475777, ISN: 0018–8689.

Athavale et al., "Coupled Electrostatics–Structures–Fluidic Simulations of A Bead Mesopump," Proceedings of the International Mechanical Engineers Congress & Exhibition, Nashville, Tennessee, Oct. 1999.

B. Halg, "On a Nonvolatile Memory Cell Based on Micro–Electro–Mechanics", Proceedings of MEMS CH2832–4/90/0000–0172 IEEE (1990), pp. 172–176.

Bertz, Schubert, Werner, "Silicon Grooves With Sidewall Angles Down to 1° made By Dry Etching", pp. 331–339.

Branebjerg, Gravesen , "A New Electrostatic Actuator Providing Improved Stroke Length and Force." Micro Electro Mechanical Systems '92 (Feb. 4–7, 1992), pp. 6–11.

Bustgens, Bacher, Menz, Schomburg, "Micropump Manufactured by Thermoplastic Molding" MEMS 1994, pp. 18–21.

C. Cabuz et al., "Factors Enhancing the Reliability of Touch–Mode Electrostatic Actuators," Sensors and Actuators 79(2000) pp. 245–250.

C. Cabuz et al., "The Double Diaphragm Pump," The 14th IEEE International Micro Electro Mechanical Systems conference, MEMS'01, Jan. 21–23, Interlachen, Switzerland.

C. Cabuz, et al., "High Reliability Touch–Mode Electrostatic Actuators", Technical Digest of the Solid State Sensor and Actuator Workshop, Hilton Head, S.C., Jun. 8–11, 1998, pp. 296–299.

C. Cabuz. Tradeoffs in MEMS Material (Invited Paper) Proceedings of the SPIE, vol. 2881, pp. 160–170, Austin, TX., Jul. 1996.

Cabuz, Cleopatra, "Electrical Phenomena at he Interface of Rolling–Contact, Electrostatic Actuators," Nanotribology: Critical Assessment and Research Needs, Kluwer Academic Publisher, pp. 221–236, Copyright 2003, presented at the Nanotribology Workshop, Mar. 13–15, 2000.

Cleo Cabuz, "Dielectric Related Effects in Micromachined Electrostatic Actuators," Annual Report of the IEEE/CEIDP Society, 1999, Annual Meeting, Austin, Texas, Oct. 17–20, 1999.

Cleopatra Cabuz et al., "Mesoscopic Sampler Based on 3D Array of Electrostatically Activated Diaphragms", The 10$^{th}$ Int. Conf. On Solid–State Sensors and Actuators, Transducers'99, Jun. 7–12, 1999, Sendai Japan, p. 1890–1.

Eric Alterndorf et al., "Results Obtained Using a Prototype Microfluidics–Based Hematology Analyzer", Department of Bioengineering, University of Washington, Box 352141, Seattle, WA 98195, dated prior to Aug. 2, 2000, pp. 73–76.

http://www.micronics.net/hfilter.htm, pp. 1–3, downloaded Jun. 14, 2000.

http://www.micronics.net/mcytometry.htm, pp. 1–4, downloaded Jun. 14, 2000.

http://www.micronics.net/orcafluidics.htm, pp. 1–4, downloaded Jun. 14, 2000.

http://www.micronics.net/tsensor.htm, pp. 1–4, downloaded Jun. 14, 2000.

Jye–Shane Yang et al., "Fluorescent Porous Polymer Films as TNT Chemosensors: Electronic and Structural Effects",J. Am. Chem. Soc., 1998, 120, pp. 11864–11873.

Jye–Shane Yang et al., "Porous Shape Persistent Fluorescent Polymer Films: An Approach to TNT Sensory Materials",J. Am. Chem. Soc., 1998, 120, pp. 5321–5322.

Lehman, J. et al., "High–Frequency Modulation Characteristics of Red VCSELs", Electronics Letters, Feb. 13, 1997, vol. 33(4), pp. 298–300. Copyright 1997 IEE.

Michael S. Freund et al., "A Chemically Diverse Conducting Polymer–Based 'Electronic Nose'", Proceedings of the National Academy of Sciences of the United States of America, vol. 92, No. 7, Mar. 28, 1995, pp. 2652–2656.

Minami K et al., "Fabrication of Distributed Electrostatic Micro Actuator (DEMA)" Journal of Microelectromechanical Systems, US, IEEE Inc., New York, vol. 2, No. 3, Sep. 1, 1993, pp. 121–127, XP000426532, ISSN: 1057–7157.

Porex Technologies, brochure, dated prior to Jun. 2, 2000, 4 pages.

Shapiro, "Practical Flow Cytometry", third edition, 1995, p. 237.

Shikida, Sato, "Characteristics of an Electrostatically–Driven Gas Valve Under High Pressure Conditions, IEEE 1994, pp. 235–240."

Shikida, Sato, Harada, "Fabrication of An S–Shaped Microactuator," Journal of Microelectromechanical Systems, vol. 6, No. 1 (Mar. 1997), pp. 18–24.

Shikida, Sato, Tanaka, Kawamura, Fujisaki, "Electrostatically Driven Gas Valve With High Conductance", Journal of Microelectromechanical Systems, vol. 3, No. 2 (Jun. 1994), pp. 76–80.

Srinivasan et al., "Self–Assembled Fluorocarbon Films for Enhanced Stiction Reduction", TRANSDUCERS '97, 1997 International Conference on Solid–State Sensors and Actuators, Chicago, Jun. 16–19, 1997, pp. 1399–1402.

Strzelecka, E. et al., "Parallel Free–Space Optical Interconnect Based on Arrays of Vertical–Cavity Lasers and Detectors with Monolithic Microlenses", Applied Optics, v. 37(14), May 10, 1998, pp. 2811–21. Copyright 1998 Optical Society of America.

T. Ohnstein et al., "Micromachined Silicon Microvalve", Proceedings of MEMS, 1990, IEEE Micro Electromechanical Systems, Napa Valley, California, Feb. 11–14, 1990, pp. 95–98.

Vandelli, et al., "Development of a MEMS Microvalve array for Fluid Flow Control," Journal of Microelectromechanical Systems, vol. 7, Dec. 4, 1998.

Wagner, Quenzer, Hoerscelmann, Lisec, Juerss, "Bistable Microvalve with Pneumatically Coupled Membranes," 0–7803–2985–6/96, IEEE (1996), pp. 384–388.

* cited by examiner

METHOD AND APPARATUS FOR RECEIVING A REMOVABLE MEDIA MEMBER

This application claims priority to U.S. provisional application No. 60/404,876, filed Aug. 21, 2002, entitled "CYTOMETER", U.S. patent application Ser. No. 09/630,924, filed Aug. 2, 2000, and entitled "PORTABLE FLOW CYTOMETER", U.S. patent application Ser. No. 09/630,927, filed Aug. 2, 2000, entitled "OPTICAL DETECTION SYSTEM FOR FLOW CYTOMETRY", U.S. patent application Ser. No. 10/174,851, filed Jun. 19, 2002, entitled "ELECTROSTATICALLY ACTUATED VALVE", and U.S. patent application Ser. No. 09/404,560, now U.S. Pat. No. 6,240,944, filed Sep. 23, 1999, entitled "ADDRESSABLE VALVE ARRAYS FOR PROPORTIONAL PRESSURE OR FLOW CONTROL", all of which are incorporated herein by reference.

BACKGROUND

The present invention generally relates to removable media, and more particularly, to methods and apparatus for receiving a removable media member.

Over the past several decades there has been an ever increasing use of devices and systems that use, in one form or another, a removable media member. Some illustrative removable media members include, for example, removable or replaceable filters, removable ink and toner cartridges, removable data storage devices such as magnetic or optical disks, removable magnetic tape cartridges, removable memory sticks, etc.

A limitation of many of the existing systems is that the alignment tolerance between the inserted removable media member and the receiving device is often not very precise. In some cases, the receiving device simply includes a slot for receiving the removable media member. In other cases, a more complex mechanical mechanism is provided, such as the mechanical mechanism used in a conventional Video Cassette Recorder (VCR) for receiving VCR tapes. For some applications, the alignment tolerance that can be achieved using these existing systems is not adequate.

Another limitation with many existing systems is that provisions are typically not made for including one or more electrical or optical devices on or in the removable media member. For some applications, however, it may be desirable to provide one or more electrical and/or optical devices on or in the removable media member. In addition, it may be desirable to provide one or more electrical, optical and/or wireless links or connections between the electrical and/or optical devices on or in the removable media and the receiving device so that, for example, various functions may be performed by the removable media member.

SUMMARY

The present invention overcomes many of the disadvantages of the prior art by providing methods and apparatus for receiving a removable media member, and more specifically, for providing tighter alignment tolerances between an inserted removable media member and a receiving device. The present invention also provides methods and apparatus for providing one or more electrical or optical device on or in the removable media member itself, and for providing an electrical and/or optical link between the one or more electrical and/or optical devices on or in the removable media and the receiving device.

In a first illustrative embodiment, an apparatus is provided for accepting a removable media member. The apparatus includes a first member and a second member, wherein the first member and the second member are adapted to move away from each other to provide a space for receiving a removable media member. Once the removable media member is inserted into the space, the first member and second member can be moved toward each other to engage and/or secure the removable media member.

In one illustrative embodiment, the first member has one or more L-shaped cleats that provide a slot to receive the removable media member. The L-shaped cleats may include, for example, a first leg that extends away from the first member and toward the second member, and a second leg that extends from a distal end of the first leg and in a perpendicular direction relative to the first leg so that a channel or receiving slot is formed. The channel or receiving slot may then receive at least one side of the removable media member.

In some embodiments, two L-shaped cleats are provided for providing two spaced channels for receiving opposing sides of the removable media member. That is, the channel or slot of the first L-shaped cleat and the channel or slot of the second L-shaped cleat may be arranged so that the removable media member slides into both channels when it is inserted between the first member and the second member. In one embodiment, the two L-shaped cleats are secured to the first member.

During use, the first member and the second member may be moved away from one another, and the removable media member may be slid into the channel or receiving slots provided by the one or more L-shaped cleats. The L-shaped cleats are preferably positioned so that that when the removable media member is received by the one or more L-shaped cleats, the removable media member is at least roughly aligned with a desired position relative to the first member and/or second member. The first member and the second member may then be moved toward one another to engage and/or secure the removable media member therebetween.

To remove the removable media member, the first member and the second member may be moved away from each other. Because at least part of the removable media member is positioned in the channel or slot of the one or more L-shaped cleats, and when the one or more L-shaped cleats are secured to the first member, the removable media member may be pulled away from the second member by the L-shaped cleats as the first member and second member are moved away from each other.

To provide better alignment between the removable media member and the first and/or second members, the second member may include one or more alignment pins that extend toward the first member. The removable media member may then include one or more receiving holes for receiving the one or more alignment pins. The alignment pins and receiving holes may provide improved alignment between the removable media member and the first and/or second members when the removable media member is secured between the first member and the second member.

Preferably, the one or more L-shaped cleats may be used to pull the removable media member away from the second member, thereby separating the one or more receiving holes of the removable media member from the one or more alignment pins that are extending from the second member. With the one or more receiving holes separated from the alignment pins, the removable media member then may be more easily removed from between the first member and the second member.

In some embodiments, the removable media member may include one or more electrical and/or optical devices. For example the removable media member may include one or more transistors, diodes, sensors such as optical, pressure, temperature and/or flow sensors, Vertical Cavity Surface Emitting Lasers (VCSELs), LEDs, electro-statically actuated actuators or pumps, micro-lenses or any other suitable electrical, mechanical and/or optical device. One illustrative removable media member that includes flow sensors is shown and described in U.S. patent application Ser. No. 10/150,851, issued as U.S. Pat. No. 6,794,981 on Sep. 21, 2004, which is incorporated herein by reference. To provide power and/or to communicate or control the one or more electrical, mechanical and/or optical devices, an electrical and/or optical interface may be provided between the first and/or second member and the removable media member.

In one illustrative embodiment, one or more electrical contact pads are provided on a surface of the removable media member. The one or more electrical contact pads may be electrically connected to the one or more electrical and/or optoelectronic devices of the removable media member, such as by a metal trace or the like. In one illustrative embodiment, the first member may include one or more spring biased probes that extend outward away from the first member and toward the second member. The one or more spring biased probes are preferably positioned to align with the one or more electrical contact pads of the removable media member when the removable media member is at a desired positioned between the first member and the second member. In some cases, the one or more alignment pins discussed above may help provide alignment between the one or more spring biased probes of the first member and the one or more electrical contact pads of the removable media member. When the first member and the second member are moved toward one another to secure and/or engage the removable media member, the one or more spring biased probes of the first member may make electrical contact with the one or more electrical contact pads of the removable media member.

To help separate the one or more spring biased probes of the first member from the one or more electrical contact pads when the first member is moved away from the second member, an outward or separating bias may be provided between the first member and the removable media member. This outward bias may be overcome when the first member and the second member are moved toward each other to secure and/or engage the removable media member. However, when the first member and the second member are moved away from each other to release the removable media member, the outward bias may separate the one or more spring biased probes of the first member from the one or more electrical contact pads, which may make the removal of the removable media member from between the first member and the second member easier and may help protect the spring bias probes from damage.

In another illustrative embodiment, one or more optical transmitters and/or receivers may be provided on a surface of the removable media member. The one or optical transmitters and/or receivers may be electrically connected to the one or more electrical and/or optoelectronic devices of the removable media member, such as by an optical waveguide, metal trace, or the like. In this embodiment, the first member and/or second member may include one or more optical transmitters and or optical receivers, which are preferably positioned to align with the one or more optical transmitters and/or receivers of the removable media member when the removable media member is at a desired positioned between the first member and the second member. In some cases, the one or more alignment pins discussed above may help provide alignment between the optical transmitters and/or optical receivers of the first and/or second members and the one or more optical transmitters and/or optical receivers of the removable media member. When the first member and the second member are moved toward one another to secure and/or engage the removable media member, the one or more optical transmitters and/or optical receivers of the first and/or second members become aligned with the one or more optical transmitters and/or optical receivers of the removable media member to provide a communications link therebetween. The one or more optical transmitters and/or optical receivers may be used to, for example, help provide optical communication between the removable media member and the receiving device that accepts or receives the removable media member. In another illustrative embodiment, one or more RF transmitters and/or receivers may be provided on or in the removable media member. The one or more RF transmitters and/or receivers may be used to, for example, help provide wireless communication between the removable media member and the receiving device that accepts or receives the removable media member.

In some cases, the removable media member may include one or more fluid ports for accepting or delivering fluid to and/or from the removable media member. In one illustrative embodiment, the removable media member may be a fluidic cartridge adapted for use in flow cytometry. The fluidic cartridge may include one or more flow channels. The one or more fluid ports may be in fluid communication with at least some of the flow channels. When so provided, one or more corresponding fluid ports may be provided on the first member and/or second member, as desired. Preferably, the one or more fluid ports of the first member and/or second member are positioned to align with at least selected ones of the fluid ports of the removable media member when the removable media member is secured and/or engaged by the first member and the second member.

In some cases, one or more alignment pins as discussed above may be provided to help provide alignment between the one or more fluid ports of the first member and/or second member and the one or more fluid ports of the removable media member. In addition, an outward bias may be provided between the removable media member and the first member and/or second member to help separate the one or more fluid ports of the first member and/or second member and the one or more fluid ports of the removable media member when the first member is moved away from the second member.

In some cases, the manufacture of the removable media member may create a ridge, a burr, or other imperfections, particularly around the outer perimeter of the removable media member. In one example, a fluidic cartridge may be manufactured by laminating several layers or sheets together, and then cutting individual fluidic cartridges from the laminated structure. At the cut lines, ridges, burrs, and other imperfections may arise. To help the removable media member seat correctly along the first and/or second member, a groove or other relief structure may provided in receiving surface of the first and/or second member to accommodate the one or more imperfections in the removable media member. In one illustrative embodiment, a groove may extend along a groove path that corresponds to, for example, the perimeter of the removable media member in anticipation of imperfections that might occur along the perimeter of the removable media member. It is contemplated, however, that a groove or other relief structure may be provided at any location where an anticipated imperfection might occur in the removable media member.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

For illustrative purposes, a portable flow cytometer system is described in detail below. However, it must be recognized that the present invention has wide applicability to numerous other removable media systems including, for example, removable or replaceable filters, removable ink and toner cartridges, removable data storage devices such as magnetic or optical disks, removable magnetic tape cartridges, removable memory sticks, as well as many other systems and/or devices that use removable media.

Figure 1:
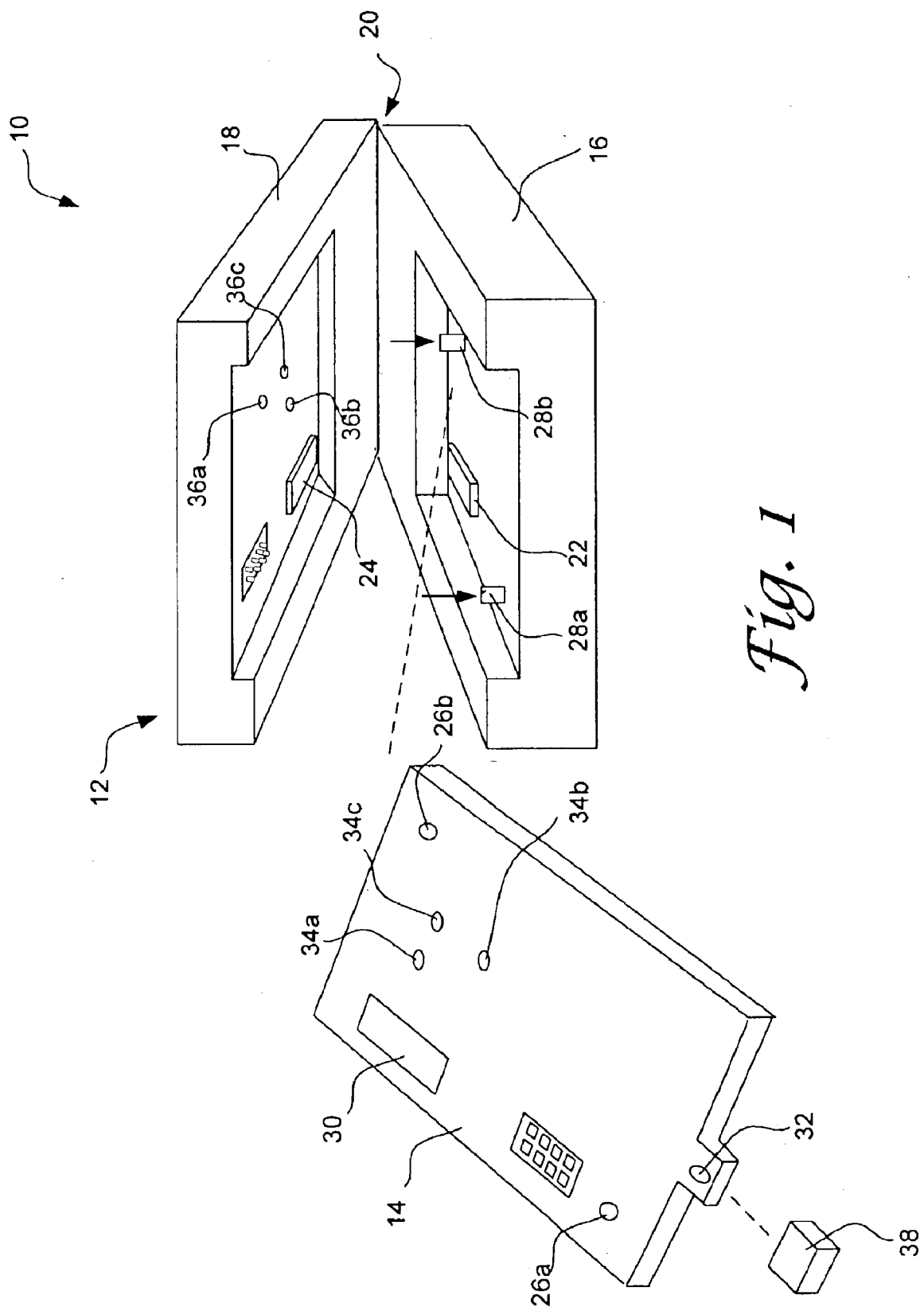
FIG. 1 is a perspective view of an illustrative portable cytometer in accordance with the present invention.

FIG. 1 is a perspective view of an illustrative portable cytometer. The portable cytometer is generally shown at 10, and includes a housing 12 and a removable or replaceable cartridge 14. The removable cartridge 14 may have a front side, a back side, and one or more lateral sides extending between the front side and the back side. The illustrative housing 12 includes a base 16, a cover 18, and a hinge 20 that attaches the base 16 to the cover 18. The base 16 includes an array of light sources 22, associated optics and the necessary electronics for operation of the cytometer. The cover 12 includes a manual pressurizing element, pressure-chambers with control microvalves, and an array of light detectors 24 with associated optics, as further described in U.S. patent application Ser. No. 09/630,924, filed Aug. 2, 2000, and entitled "PORTABLE FLOW CYTOMETER", and U.S. patent application Ser. No. 09/630,927, filed Aug. 2, 2000, and entitled "OPTICAL DETECTION SYSTEM FOR FLOW CYTOMETRY", both of which are incorporated herein by reference.

The removable member (e.g. cartridge) 14 preferably receives a sample fluid via a sample collector port 32. A cap 38 may be used to protect the sample collector port 32 when the removable cartridge 14 is not in use. The removable cartridge 14 may perform blood dilution, red cell lysing, and hydrodynamic focusing for core formation. The removable cartridge 14 may be constructed similar to the fluidic circuits available from Micronics Inc., some of which are fabricated using a laminated structure with etched fluid channels.

The removable cartridge 14 is inserted into the housing when the cover 18 is in the open position. The removable cartridge 14 may include holes 26a and 26b for receiving registration pins 28a and 28b in the base 16, which help provide alignment and coupling between the different parts of the instrument. The removable cartridge 14 also preferably includes a transparent flow stream window 30, which is in alignment with the array of the light sources 22 and light detectors 24. When the cover is moved to the closed position, and the system is pressurized, the cover 18 provides controlled pressures to pressure receiving ports 34a, 34b, and 34c in the removable cartridge 14 via pressure providing ports 36a, 36b and 36c, respectively.

To initiate a test, the cover 18 is lifted and a new cartridge 14 is placed and registered onto the base 16. A blood sample is introduced into the sample collector 32. The cover 18 is closed and the system is manually pressurized. Once pressurized, the instrument performs a white blood cell cytometry measurement. The removable cartridge 14 provides blood dilution, red cell lysing, and hydrodynamic focusing for core formation. The light sources 22, light detectors 24 and associated control and processing electronics perform differentiation and counting of white blood cells based on light scattering signals received by the light detectors 24. Rather than using a hinged construction for the housing 12, it is contemplated that a sliding cartridge slot or any other suitable construction may be used, including that described further below with respect to FIGS. 5–12.

Figure 2:
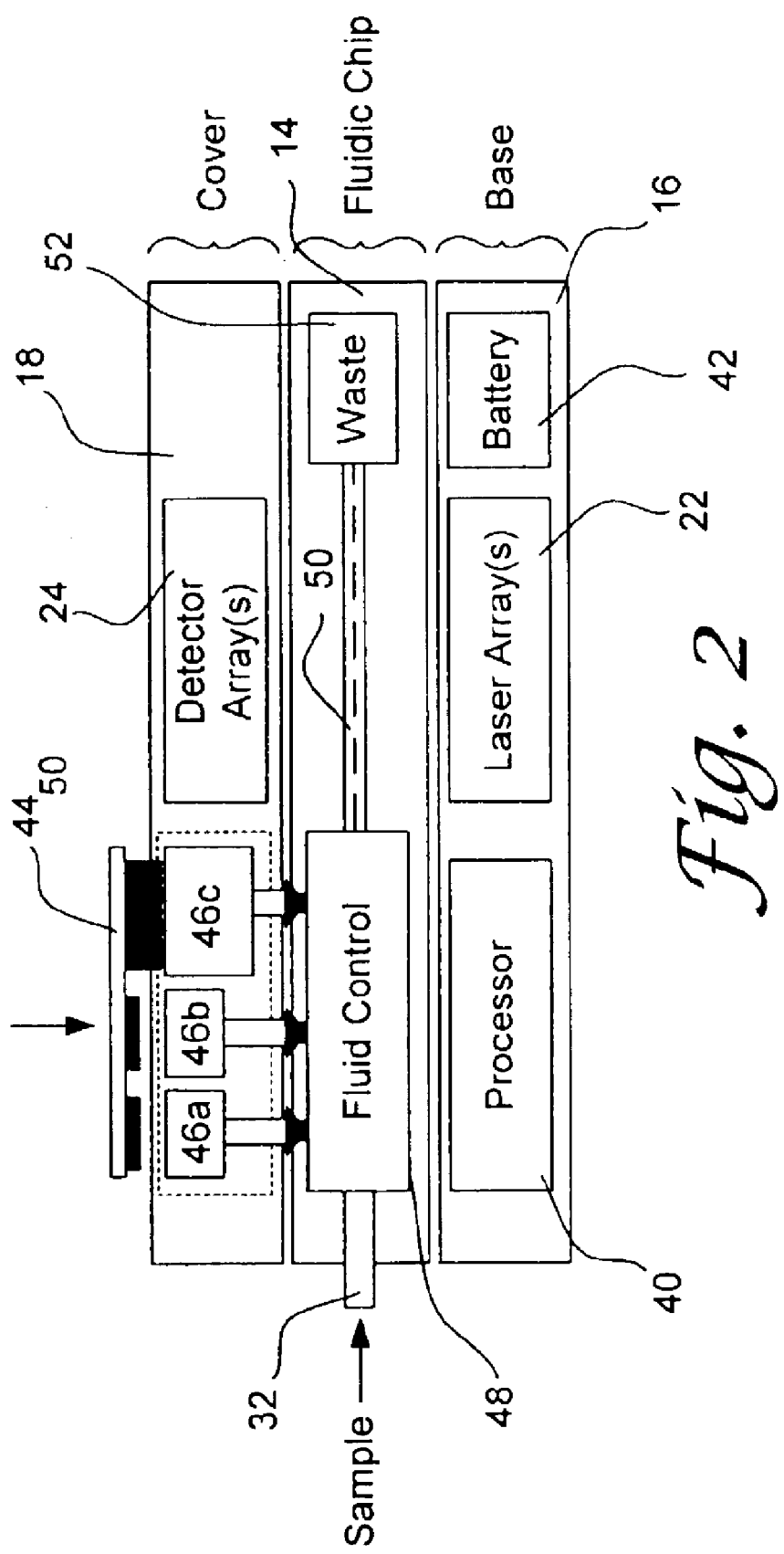
FIG. 2 is a schematic view of the illustrative portable cytometer of FIG. 1.

FIG. 2 is a schematic view of the illustrative portable cytometer of FIG. 1. As above, the base 16 may include an array of light sources 22, associated optics and the necessary control and processing electronics 40 for operation of the cytometer. The base 16 may also include a battery 42 for powering the cytometer. The cover 12 is shown having a manual pressurizing element 44, pressure-chambers 46a, 46b and 46c with control microvalves, and an array of light detectors 24 with associated optics.

The removable cartridge 14 may receive a sample fluid via the sample collector port 32. When pressurized by the cover 18, the removable cartridge 14 performs blood dilution, red cell lysing, and hydrodynamic focusing for core formation in a preferred embodiment. Once formed, the core is provided down a flow stream path 50, which passes the flow stream window 30 of FIG. 1. The array of light sources 22 and associated optics in the base provide light through the core stream via the flow stream window 30. The array of light detectors and associated optics receive scattered and non-scattered light from the core, also via the flow stream window 30. The controller or processor 40 receives output signals from the array of detectors, and differentiates and counts selected white blood cells that are present in the core stream.

It is contemplated that the removable cartridge 14 may include a fluid control block 48 for helping to control the velocity of each of the fluids. In the illustrative embodiment, the fluid control block 48 includes flow sensors for sensing the velocity of the various fluids and report the velocities to the controller or processor 40. The controller or processor 40 may then adjust the microvalves associated with pressure-chambers 46a, 46b and 46c to achieve the desired pressures and thus desired fluid velocities for proper operation of the cytometer. In some embodiments, and as further described below, one or more electrical, optical and/or wireless connections may be provided between the processor 40 in the base 16 and the flow sensors on the removable cartridge 14.

Because blood and other biological waste can spread disease, the removable cartridge 14 preferably has a waste reservoir 52 downstream of the flow stream window 30. The waste reservoir 52 receives and stores the fluid of the flow stream in the removable cartridge 14. When a test is completed, the removable cartridge may be removed and disposed of, preferably in a container compatible with biological waste.

Figure 3:
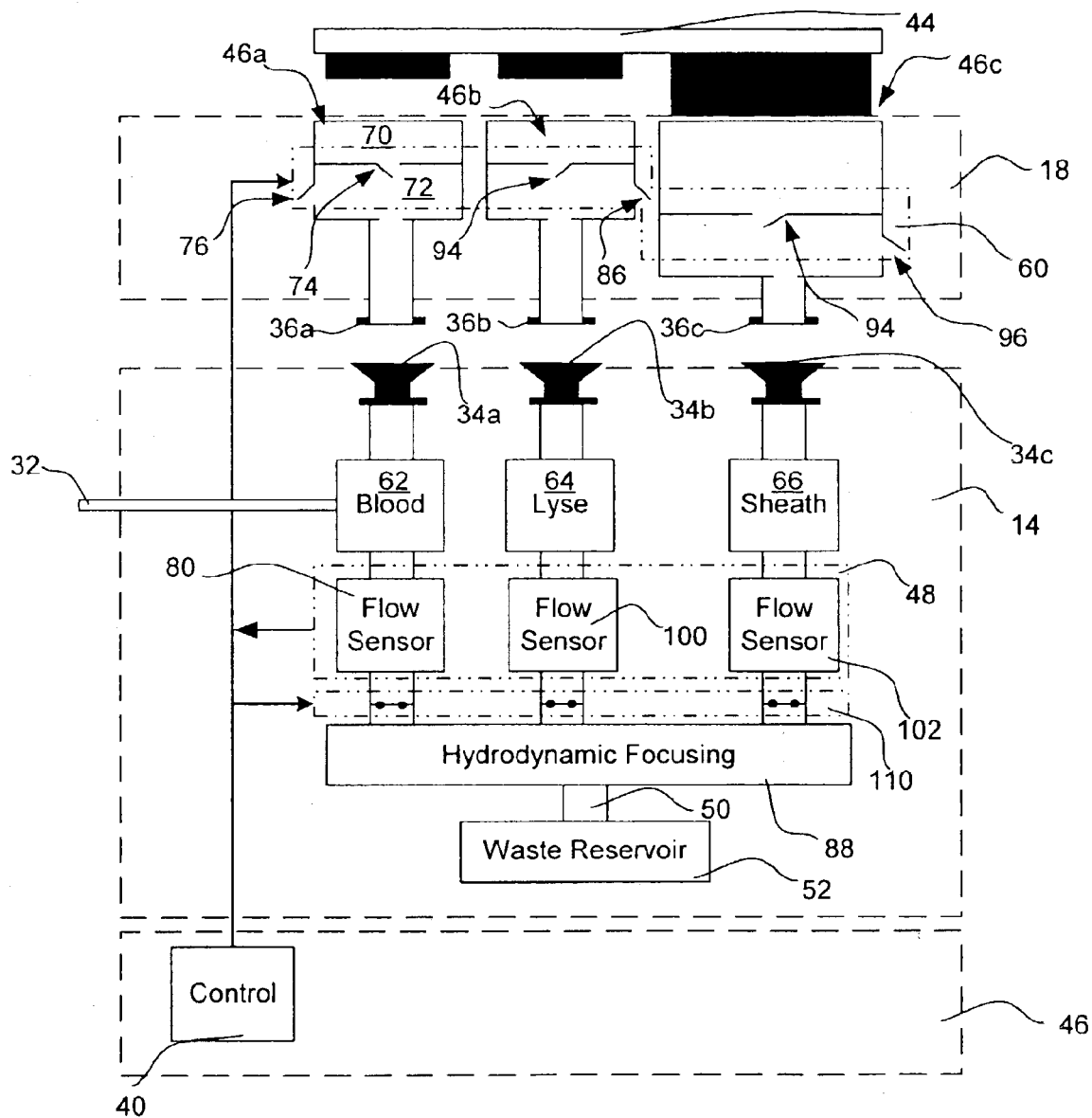
FIG. 3 is a more detailed schematic diagram showing the portable cytometer of FIG. 2 with the cover not yet depressed.
Figure 4:
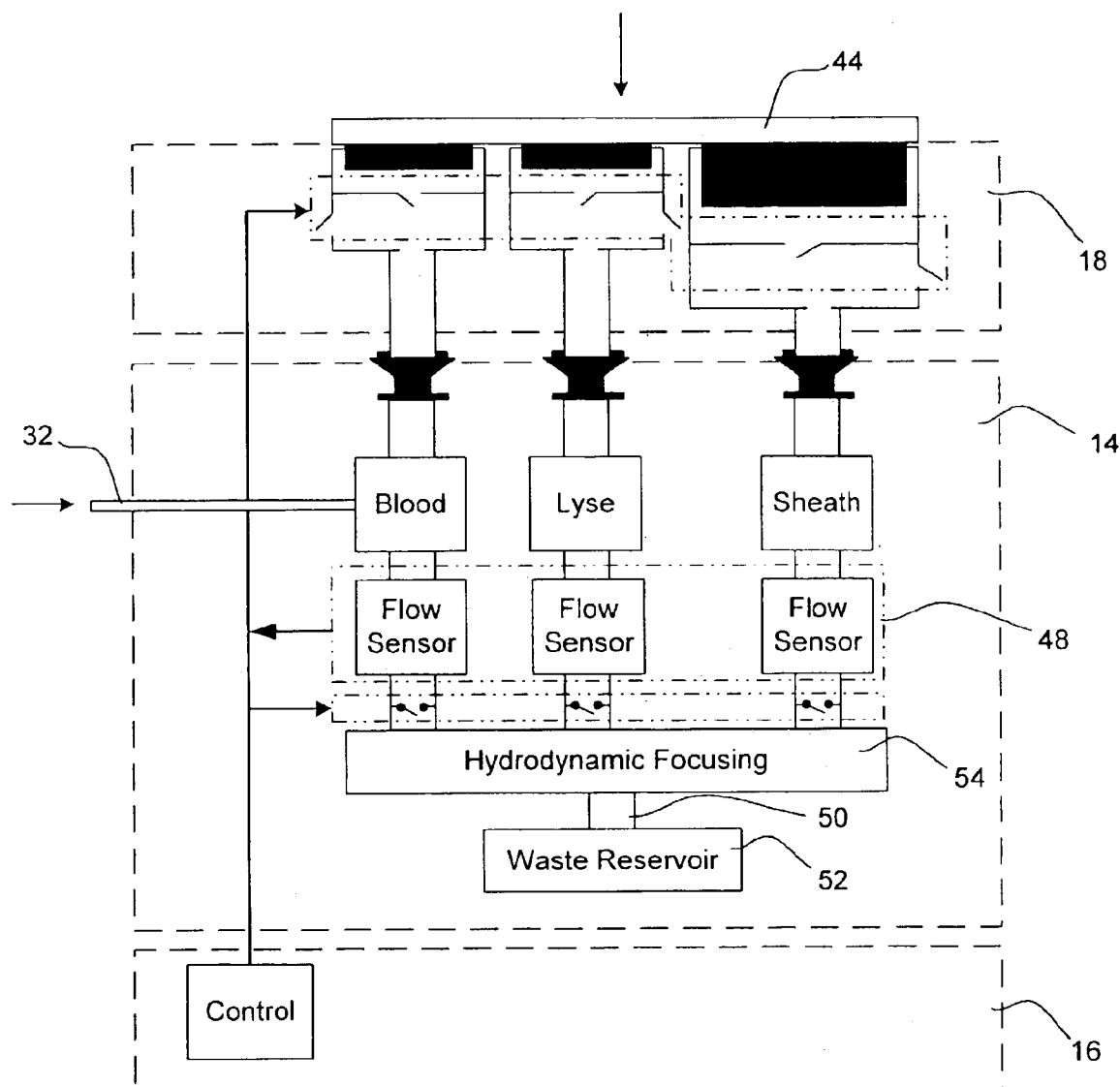
FIG. 4 is a more detailed schematic diagram showing the portable cytometer of FIG. 2 with the cover depressed.

FIG. 3 is a more detailed schematic diagram showing the portable cytometer of FIG. 2 with the cover 18 not yet depressed. FIG. 4 is a more detailed schematic diagram showing the portable cytometer of FIG. 2 with the cover depressed. The cover 18 is shown having a manual pressurizing element 44, pressure-chambers 46a, 46b and 46c, and control microvalves generally shown at 60. The array of light sources and detectors are not shown in these Figures.

There are three pressure chambers 46a, 46b and 46c, one for each fluid to be pressurized. In the illustrative embodiment, pressure chamber 46a provides pressure to a blood sample reservoir 62, pressure chamber 46b provides pressure to a lyse reservoir 64, and pressure chamber 46c provides pressure to a sheath reservoir 66. The size and shape of each pressure chamber 46a, 46b and 46c may be tailored to provide the desired pressure characteristics to the corresponding fluid.

Pressure chamber 46a includes a first pressure chamber 70 and a second pressure chamber 72. A first valve 74 is provided between the first pressure chamber 70 and the second pressure chamber 72 for controllably releasing the pressure in the first pressure chamber 70 to a second pressure chamber 72. A second valve 76, in fluid communication with the second pressure chamber 72, controllably vents the pressure in the second pressure chamber 72. Each valve is preferably an array of electrostatically actuated microvalves that are individually addressable and controllable, as described in, for example, co-pending U.S. patent application Ser. No. 09/404,560, entitled "ADDRESSABLE VALVE ARRAYS FOR PROPORTIONAL PRESSURE OR FLOW CONTROL", and incorporated herein by reference. Pressure chambers 46b and 46c include similar valves to control the pressures applied to the lyse reservoir 64 and sheath reservoir 66, respectively. Alternatively, each valve may be an array of electrostatically actuated microvalves that are pulse modulated with a controllable duty cycle to achieve a controlled "effective" flow or leak rate. Alternatively, each valve may be a similar to that described in co-pending U.S. patent application Ser. No. 10/174,851, entitled "ELECTROSTATICALLY ACTUATED VALVE", which is incorporated herein by reference.

The removable cartridge 14 has pressure receiving ports 34a, 34b, and 34c for receiving the controlled pressures from the cover 18. The controlled pressures are provided to the blood reservoir 62, lyse reservoir 64 and sheath reservoir 66, as shown. The lyse reservoir 64 and sheath reservoir 66 are preferably filled before the removable cartridge 14 is shipped for use, while the blood reservoir 62 is filled from sample collector port 32. A blood sample may be provided to the sample collector port 32, and through capillary action, the blood sample may be drawn into the blood reservoir 62. Once the blood sample is in the blood reservoir 62, the cover 18 may be closed and the system may be pressurized.

A flow sensor is provided in-line with each fluid prior to hydrodynamic focussing. Each flow sensor 80, 100 and 102 measures the velocity of the corresponding fluid. The flow sensors are preferably thermal anemometer type flow sensors, and more preferably microbridge or microbrick type flow sensor. Microbridge flow sensors are described in, for example, U.S. Pat. No. 4,478,076, U.S. Pat. No. 4,478,077, U.S. Pat. No. 4,501,144, U.S. Pat. No. 4,651,564, U.S. Pat. No. 4,683,159, and U.S. Pat. No. 5,050,429, all of which are incorporated herein by reference. An output signal from each flow sensor 80, 100 and 102 is provided to controller or processor 40 via one or more electrical connection between the removable cartridge and the base. Alternatively, or in addition, one or more optical transmitters and/or optical receivers may be provided on the removable cartridge 14. The one or more optical transmitters and/or optical receivers may be used to, for example, help provide optical communication between the removable cartridge 14 and the controller or processor 40 in the base 16. Likewise, and in some embodiments, one or more RF transmitters and/or receivers may be provided on or in the removable cartridge. The one or more RF transmitters and/or receivers may be used to, for example, help provide wireless communication between the removable cartridge and the base 16.

The controller or processor 40 opens the first valve 74 when the velocity of the blood sample drops below a first predetermined value and opens the second valve 76 when the velocity of the blood sample increases above a second predetermined value. Valves 84, 86, 94 and 96 operate in a similar manner to control the velocities of the lyse and sheath fluids.

During operation, and to pressurize the system, the manual pressurizing element 44 is depressed. In the example shown, the manual pressurizing element 44 includes three plungers, with each plunger received within a corresponding one of the first pressure chambers. The plungers create a relatively high non-precision pressure in the first pressure chambers. Lower, controlled pressures are built in the secondary chambers by opening the first valves 70, 84 and 94, which produce a controllable leak into the secondary chambers. If too much pressure builds up in the secondary pressure chambers, the corresponding vent valve 76, 86 and 96 are opened to relieve the pressure.

When closing the cover 18, the normally open first valves 74, 84 and 94 are closed while the vent valves 76, 86 and 96 are open. When a predetermined pressure P is achieved in the first pressure chambers, the vent valves 76, 86 and 96 are closed, and the first valves 74, 84 and 94 are opened to build a lower pressure P' in the secondary pressure chambers. The controlled pressure in the secondary pressure chambers provide the necessary pressures to the fluidic circuit of the removable cartridge 14 to produce fluid flow for the blood, lyse and sheath. The velocity of the fluid flow is then measured by the downstream flow sensors 80, 100 and 102. Each flow sensor provides an output signal that is used by the controller or processor 40 to control the operation of the corresponding first valve and vent valve to provide a desired and constant flow rate for each fluid.

Downstream valves generally shown at 110 may also be provided. Controller or processor 40 may close downstream valves 110 until the system is pressurized. This may help prevent the blood, lyse and sheath from flowing into the fluid circuit before the circuit is pressurized. In another embodiment, downstream valves 110 are opened by mechanical action when the cover is closed.

In some embodiments, pressure generated in pressure-chambers 46a, 46b or 46c, or some other pressure chamber (not shown), may be used to control one or more pneumatic valves placed on or in the removable cartridge 14. The one or more pneumatic valves may be used to control, for example, a flow path, a flow rate or some other flow property associated with a fluid or gas on or in the removable cartridge 14. Alternatively, or in addition, the pressure generated in pressure-chambers 46a, 46b or 46c, or some other pressure chamber (not shown), may be used to control one or more pneumatically controlled elements that provide some other mechanical movement on or in the removable cartridge 14, such as a pneumatically controlled pump, plunger, gear, etc.

Figure 5:
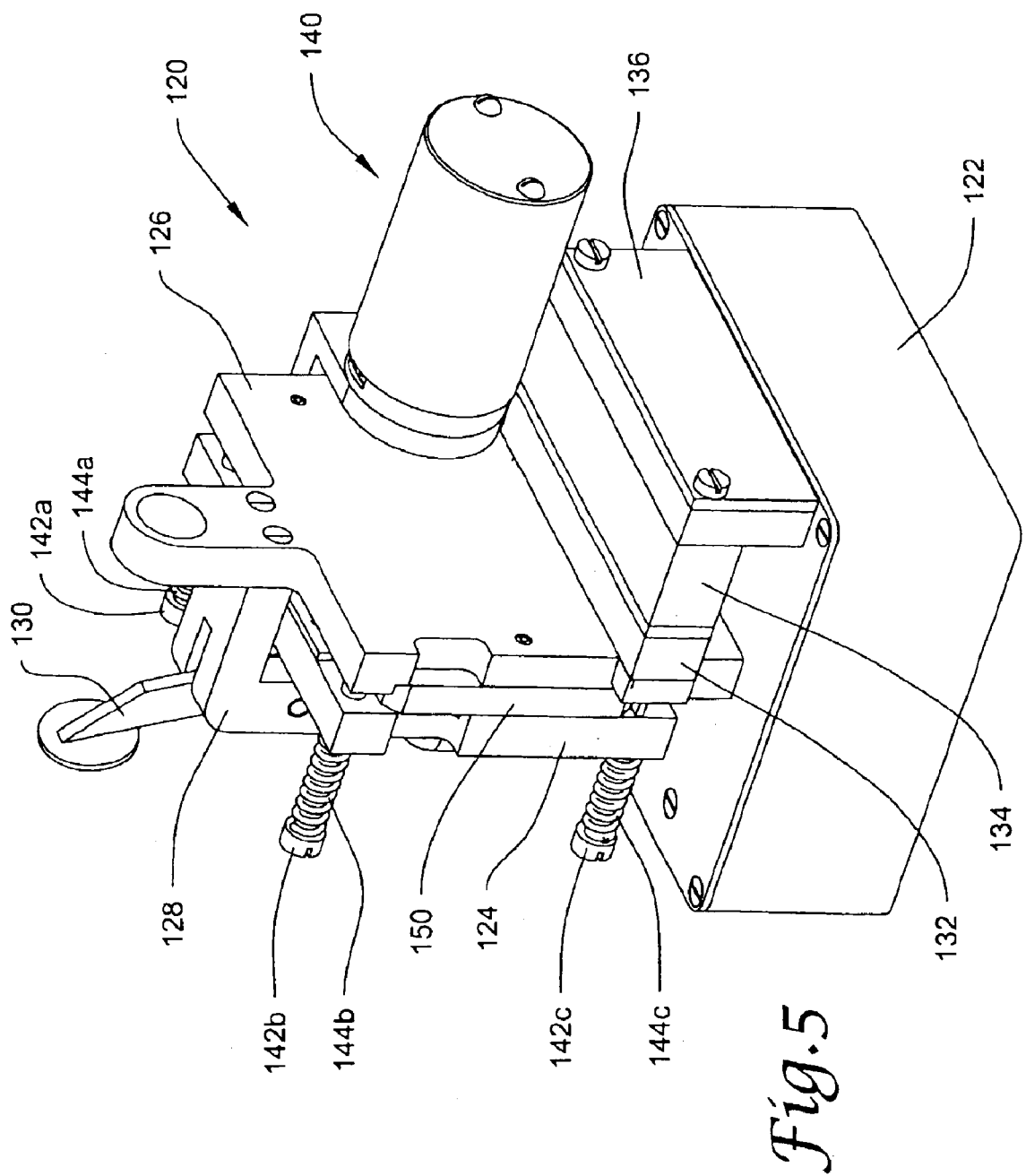
FIG. 5 is a perspective view of another illustrative portable cytometer in accordance with the present invention.

FIG. 5 is a perspective view of another illustrative portable cytometer in accordance with the present invention. The basic operation of the portable cytometer of FIG. 5 is similar to that described above with respect to FIGS. 1-4 above. The portable cytometer of FIG. 5 is generally shown at 120, and includes a base 122, a first member 124, a second member 126, a clamp frame 128 with clamp lever 130, an air buffer module 132, a valve module assembly 134 with polymer microvalves, an air accumulator module 136, and an optics assembly 140.

In the illustrative embodiment, the second member 126 is fixed to the base 122. A number of shoulder screws 142a, 142b, 142c and 142d (142d not shown in FIG. 5) pass through holes in the first member 124 and are secured to the second member 126. Springs 144a, 144b, 144c and 144d (144d not shown in FIG. 5) are placed between the first member 124 and the head of the corresponding shoulder screw 142a, 142b, 142c and 142d. The springs 144a, 144b, 144c and 144d provide a bias force to the first member 124 toward the second member 126.

The clamp frame 128 is secured to the second member 126 as shown. The clamp lever 130 interacts with the clamp frame to provide an outward bias force to the first member away from the second member 126. By moving the clamp lever 130 in a first direction, the first member 124 is moved away from the second member 126 by overcoming the inward bias force provided of spring 144a, 144b, 144c and 144d. By moving the clamp lever 130 in a second opposite direction, the first member 124 is moved toward the second member 126, assisted by the inward bias force provided of spring 144a, 144b, 144c and 144d.

Figure 6:
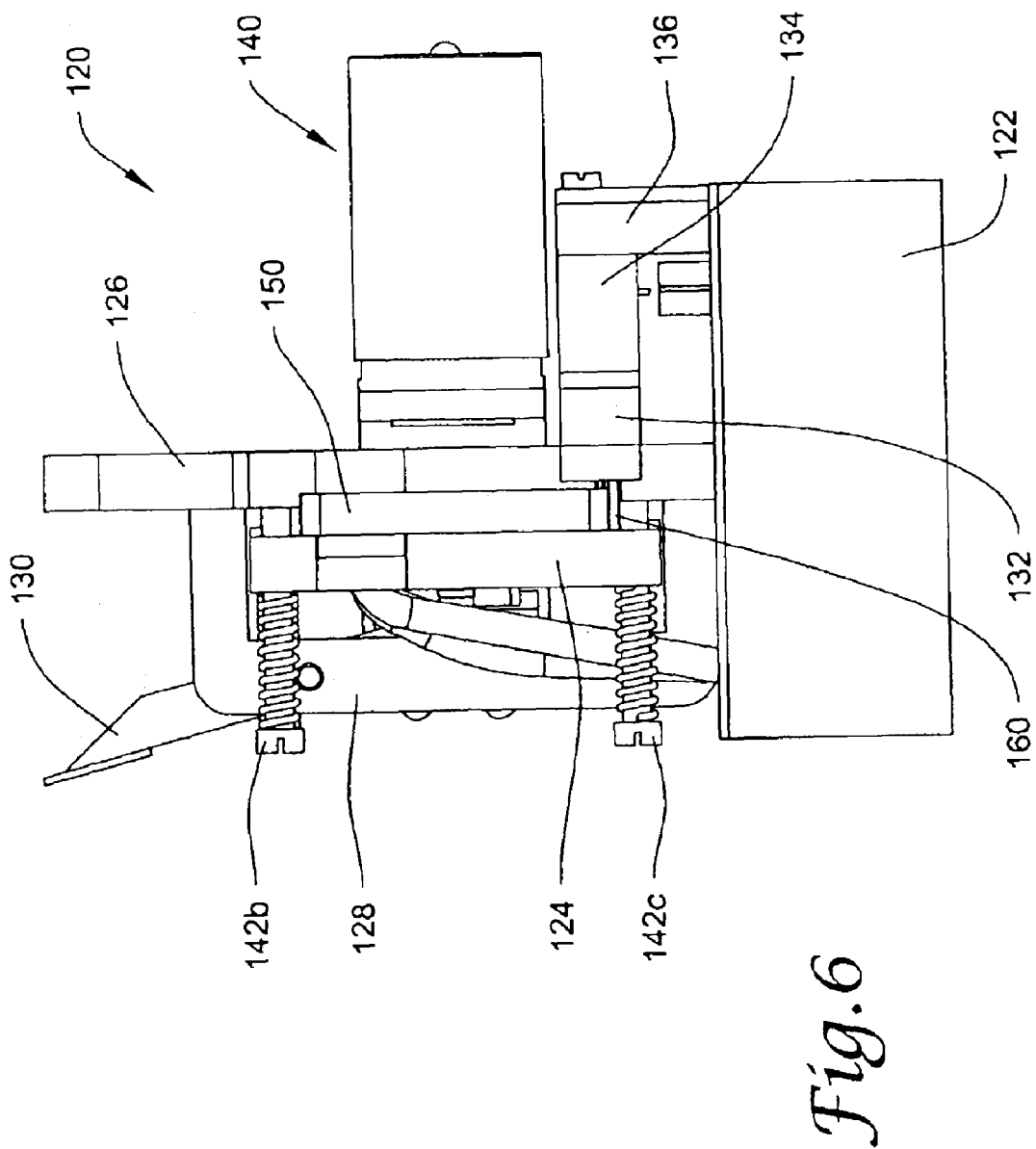
FIG. 6 is a perspective side view of the illustrative portable cytometer of FIG. 5.

During operation, the clamp lever 130 may be moved in the first direction to move the first member 124 away from the second member 126, leaving a space therebetween. A removable media member, such as a removable fluidic cartridge 150, may then be slid into the space. The removable cartridge 150 may have a front side, a back side, and one or more lateral sides extending between the front side and the back side, as shown. The clamp lever 130 may then be moved in the second direction to move the first member 124 toward the second member 136 to secure and/or engage the removable media member 150, as shown in FIG. 5. FIG. 6 is a perspective side view of the illustrative portable cytometer of FIG. 5.

In one illustrative embodiment, the removable media member 150 has one or more fluid ports in the front and/or back sides, similar to that described above with respect to FIGS. 1-4. It is contemplated that the one or more fluid ports may be adapted to accept either a gas or a liquid, depending on the application. The second member 126 of the illustrative embodiment includes corresponding fluid ports that align with the one or more fluid ports of the removable media member 150. One such fluid port is shown at 160 in FIG. 6. A fluid port gasket (see FIG. 12 below) may be secured to the second member 126 to help provide a better seal, if desired.

A fluid control module may then be fluidly coupled to the fluid ports of the second member 126. In the illustrative embodiment, the fluid control module includes the air accumulator module 136, the valve module assembly 134 with polymer microvalves, and the air buffer module 132. The air accumulator module 136 includes an internal chamber for accumulating an pressure. A port (not shown) may be provided from the internal chamber of the air accumulator 136 to an air pressure source. The accumulated air pressure may be supplied to the valve module assembly 134. The valve module assembly may include one or more microvalves, such as polymer microvalves as disclosed in U.S. patent application Ser. No. 10/174.851, entitled "ELECTROSTATICALLY ACTUATED VALVE", which is incorporated herein by reference. In the illustrative embodiment, the valve module assembly 134 may provide three separate pressure channels including a blood channel, a lyse channel and a sheath channel, as shown and described above with respect to FIGS. 1-4. The valve module assembly 134 is preferably controlled by a controller in base 122 to provide three separate controlled pressures to air buffer module 132. Air buffer module 132 buffers the controlled pressures, and delivers the pressurized air to the fluid ports of the removable media member 150 via the fluid ports that pass in or through the second member 126.

In some cases, the removable media member 150 may include one or more electrical and/or optical devices. For example, and in the illustrative embodiment, the removable media member 150 may include three flow sensors, with each flow sensor measuring the flow rate of the pressurized fluid through one of the three separate pressure channels of the removable media member 150. Like above, the flow sensors are preferably thermal anemometer type flow sensors, and more preferably microbridge or microbrick type flow sensor, commercially available from Honeywell International. Microbridge flow sensors are described in, for example, U.S. Pat. No. 4,478,076, U.S. Pat. No. 4,478,077, U.S. Pat. No. 4,501,144, U.S. Pat. No. 4,651,564, U.S. Pat. No. 4,683,159, and U.S. Pat. No. 5,050,429, all of which are incorporated herein by reference. An output signal from each flow sensor is provided to controller or processor in base 122, preferably via an electrical, optical and/or wireless coupling between the removable media member and the second member 126.

The optical assembly module 140 preferably includes one or more light sources (e.g. VCSELs) on one side of the removable cartridge 150, one or more light detectors on the opposite side of the removable cartridge 150, and associated optics. When so provided, the removable cartridge 150 may include a transparent flow stream window, which is in alignment with the one or more light sources and one or more light detectors. The air buffer module 132, valve module assembly 134, and air accumulator module 136 are preferably controlled to form a core stream down a flow stream path that passes the flow stream window in the removable cartridge 150. The light sources, when activated, provide light through the core stream via one side of the flow stream window. The optical detectors receive scattered and non-scattered light from the core stream via the opposite side of the flow stream window. A controller or processor in the base 122 then receives output signals from the detectors, and differentiates and counts selected white blood cells that are present in the core stream.

Figure 7:
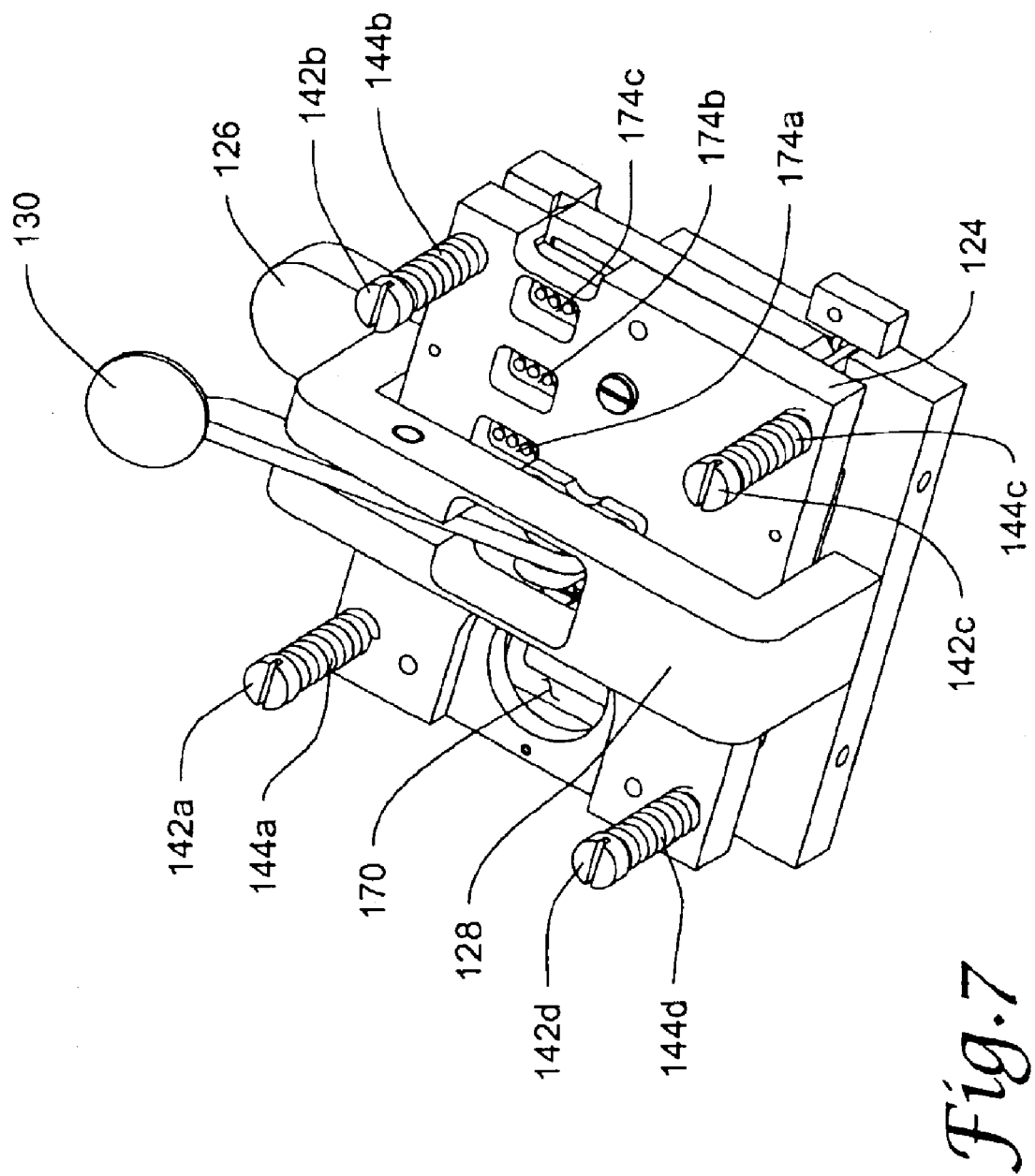
FIG. 7 is another perspective view of the illustrative portable cytometer of FIG. 5.

FIG. 7 is another perspective view of the illustrative portable cytometer of FIG. 5, further illustrating additional detail. FIG. 7 shows a hole 170 through the first member 124 and second member 126. The hole 170 may allow the one or more light sources and one or more light detectors of the optical assembly module 140 to directly access the flow stream window of the removable cartridge (not shown in FIG. 7).

FIG. 7 also shows one or more spring biased probes secured to the first member 124. The one or more spring biased probes are preferably positioned to align with the one or more electrical contact pads on the removable cartridge when the removable cartridge is at a desired positioned between the first member 124 and the second member 126. In the illustrative embodiment, three arrays of spring biased probes 174a, 174b and 174c are provided, with each array mounted via a small PC board and secured within a corresponding hole in the first member 124. The holes in the first member 124 may provide access to the reverse side of the spring bias probes, which in some embodiments, may provide a convenient location to make an electrical connection between a controller in the base 122 and each spring bias probe.

In addition, or alternatively, it is contemplated that one or more optical transmitters and/or optical detectors may be secured to the first and/or second member. The one or more optical transmitters and/or optical detectors are preferably positioned to align with the one or more optical detectors and/or optical transmitters on the removable cartridge when the removable cartridge is at a desired positioned between the first member 124 and the second member 126. This may provide an optical link between the removable cartridge and the first member and/or second member 126, as desired.

Figure 8:
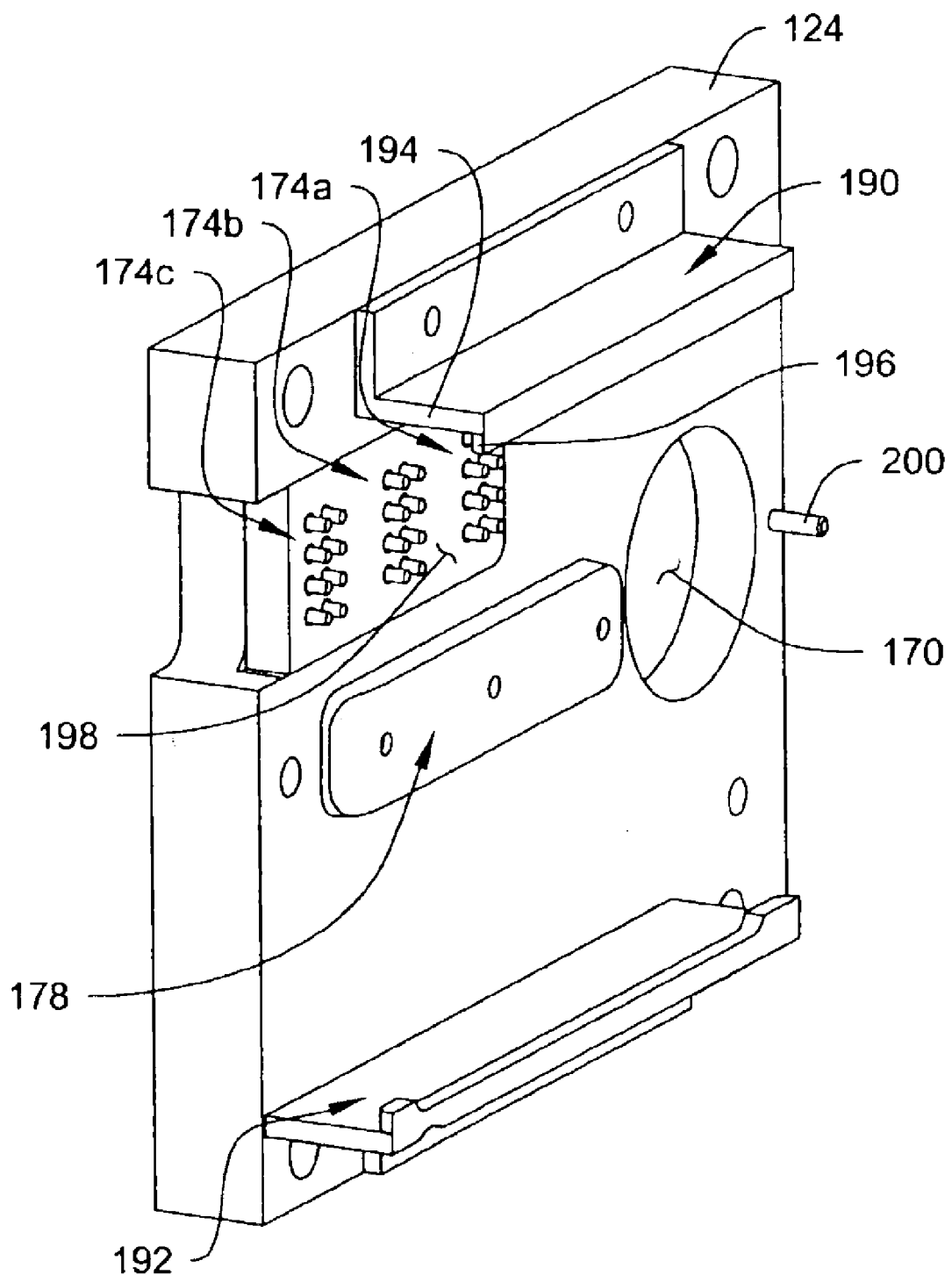
FIG. 8 is a perspective view of the first plate or member of the illustrative portable cytometer of FIG. 5.

FIG. 8 is a perspective view of the first member 124 of the illustrative portable cytometer of FIG. 5. FIG. 8 shows the opposite side of the three arrays of spring biased probes 174a, 174b and 174c of FIG. 7. As can be seen, each spring bias probes is biased by a spring in an outward direction away from the first member 124 and toward the removable cartridge (not shown in FIG. 8). The spring biased probes are preferably positioned to align with the one or more electrical contact pads on the removable cartridge when the removable cartridge is at a desired positioned between the first member 124 and the second member 126. When the first member 124 and the second member 126 are moved toward one another to secure and/or engage the removable cartridge, the spring biased probes preferably make electrical contact with the one or more electrical contact pads on the removable cartridge.

Figure 11:
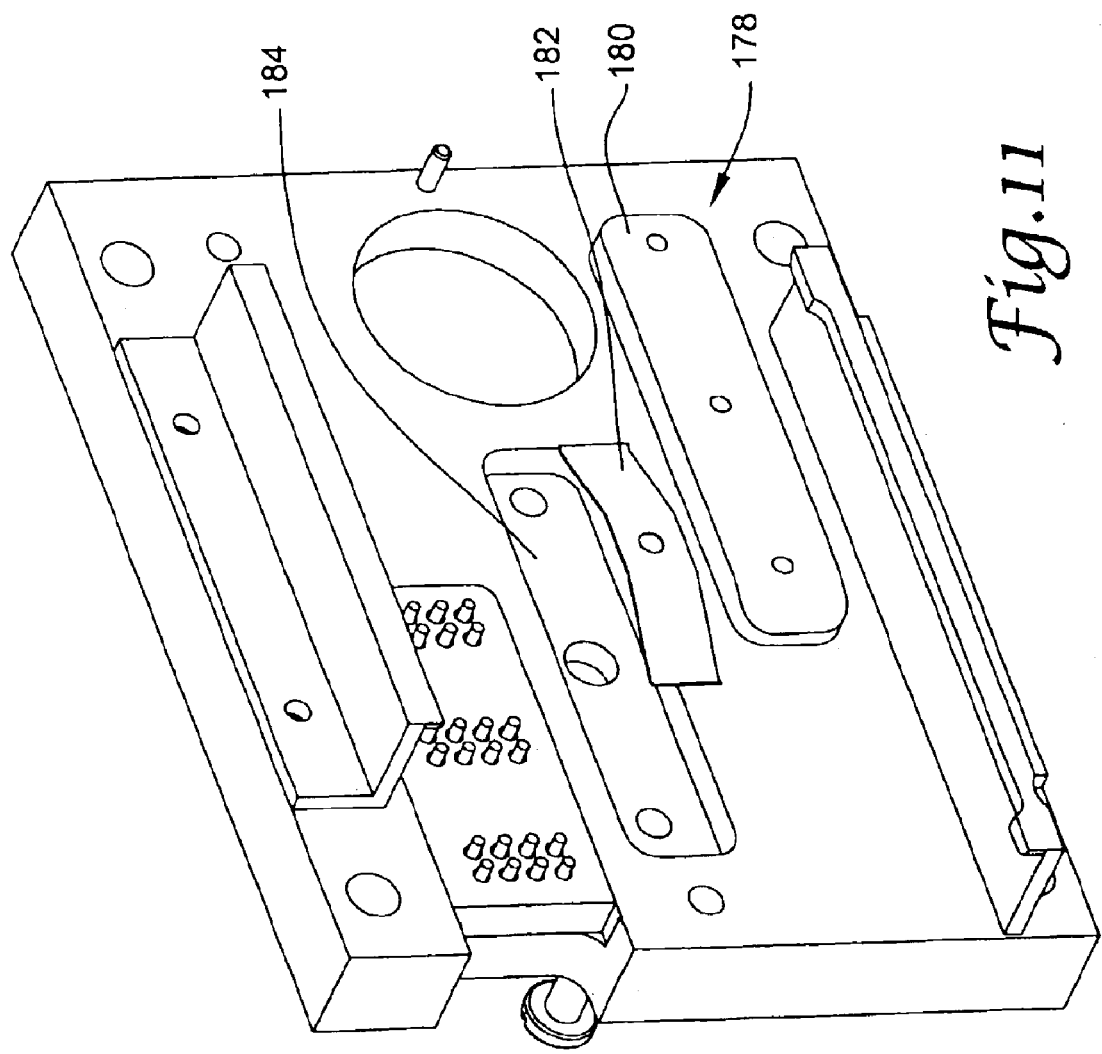
FIG. 11 is a perspective view of the outward bias wedge of the first plate or member of FIG. 8.

To help separate the spring biased probes from the one or more electrical contact pads on the removable cartridge when the first member 124 is moved away from the second member 126, an outward or separating bias 178 may be provided between the first member 124 and the removable cartridge. Referring momentarily to FIG. 11, the outward bias 178 may include a wedge 180 and a spring 182. The spring 182 may be positioned in a recess 184 in the first member 124, with the wedge 180 biased in an outward direction by the spring 182.

Referring back to FIG. 8, the outward bias 178 may be overcome when the first member 124 and the second member 126 are moved toward each other to secure and/or engage the removable cartridge. However, when the first member 124 and the second member 126 are moved away from each other to release the removable cartridge, the outward bias 178 may separate the one or more spring biased probes 174a, 174b and 174c from the one or more electrical contact pads of the removable cartridge, which may make the removal of the removable cartridge from between the first member 124 and the second member 126 easier and may help protect the spring bias probes from damage during the removal process.

The first member 124 may also have one or more L-shaped cleats that provide a slot to receive the removable cartridge. In the illustrative embodiment of FIG. 8, an upper L-shaped cleat 190 and a lower L-shaped cleat 192 are provided. The L-shaped cleats 190 and 192 may each include, for example, a first leg 194 that extends away from the first member 124 and toward the second member, and a second leg 196 that extends from a distal end of the first leg 194 and in a perpendicular direction relative to the first leg 194 so that a channel or receiving slot 198 is formed. The channel or receiving slot 198 may then receive one side of the removable media member. In the illustrative embodiment, the upper L-shaped cleat 190 includes a second leg 196 that extends in a downward direction, and the lower L-shaped cleat 192 includes a second leg that extends in an upward direction. In addition, the upper L-shaped cleat 190 and the lower L-shaped cleat 192 are spaced so that two spaced channels 196 are provided for receiving opposing sides (e.g. upper side and lower side) of the removable cartridge. That is, the channel or slot of the upper L-shaped cleat 190 and the channel or slot of the lower L-shaped cleat 192 are arranged so that the removable cartridge slides into both channels when it is inserted between the first member 124 and the second member 126. In the illustrative embodiment, the two L-shaped cleats are secured to the first member 124.

An alignment pin 200 may be provided toward the back of the first member 124 to engage the back of the removable cartridge. The alignment pin 200 is preferably positioned to stop the removable cartridge at or near the desired insertion position between the first member 124 and the second member 126.

During use, the first member 124 and the second member 126 may be moved away from one another, and the removable cartridge may be slid into the channel or receiving slots 198 provided by the L-shaped cleats 190 and 192 until the removable cartridge engages the alignment pin 200. The L-shaped cleats 190 and 192 are preferably positioned so that that when the removable cartridge is received by the L-shaped cleats 190 and 192, the removable cartridge is at least roughly aligned with a desired position relative to the first member 124 and/or second member 126. The first member 124 and the second member 126 may then be moved toward one another to engage and/or secure the removable cartridge therebetween.

To remove the removable cartridge, the first member 124 and the second member 126 may be moved away from each other. Because the upper and lower edges of the removable cartridge are positioned in the channel or slot 198 of the L-shaped cleats 190 and 192, the removable cartridge is pulled away from the second member 126 by the second legs 196 of the L-shaped cleats 190 and 192 as the first member 124 and second member 126 are moved away from each other.

Figure 12:
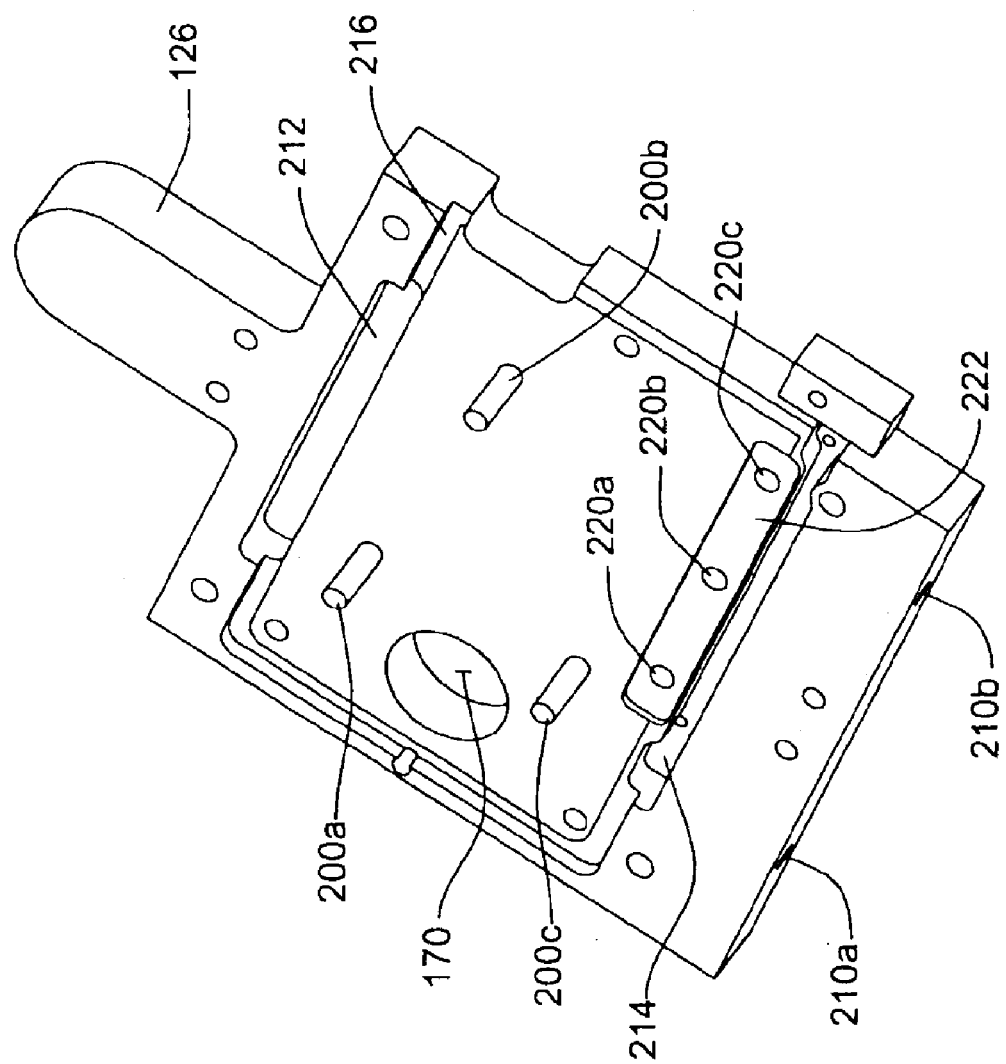
FIG. 12 is a perspective view of the second plate or member of the illustrative portable cytometer of FIG. 5.

To provide better alignment between the removable media member and the first member 124 and/or the second members 126, the second member 126 may include one or more alignment pins 200a–200c that extend toward the first member (see FIG. 12). The removable media member 150 may then include one or more receiving holes for receiving the one or more alignment pins 200a–200c. The alignment pins 200a–200c and receiving holes may provide improved alignment between the removable media member 150 and the first member 124 and/or second member 126 when the removable media member 150 is secured between the first member 124 and the second member 126.

Preferably, the L-shaped cleats 190 and 192 may be used to pull the removable media member 150 away from the second member 126, thereby separating the one or more receiving holes of the removable media member 150 from the one or more alignment pins 200a–200c that are extending from the second member 126. With the one or more receiving holes separated from the alignment pins 200a–200c, the removable media member 150 then may be more easily removed from between the first member 124 and the second member 126.

Figure 9:
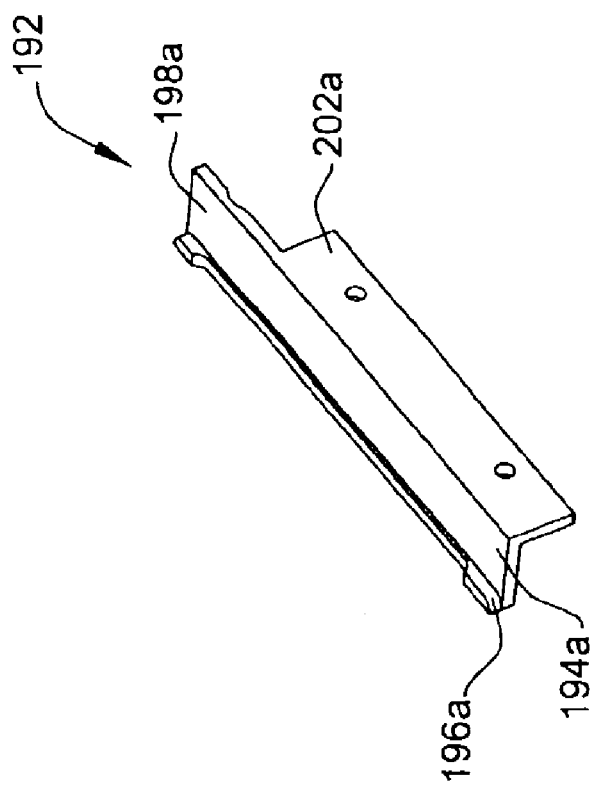
FIG. 9 is a perspective view of the lower cleat of the first plate or member of FIG. 8.

FIG. 9 is a perspective view of the lower cleat 192 of FIG. 8. The illustrative lower cleat 192 includes a first leg 194a and a second leg 196a, wherein the second leg 196a extends from a distal end of the first leg 194a and in a perpendicular direction to form a channel or receiving slot 198a. A mounting leg 202a may extend from the first leg 194 as shown, for mounting the lower cleat 192 to the first member 124.

Figure 10:
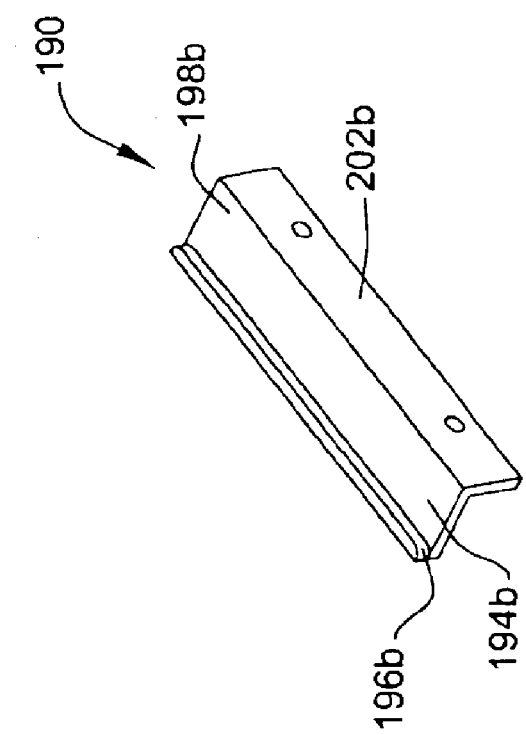
FIG. 10 is a perspective view of the upper cleat of the first plate or member of FIG. 8.

FIG. 10 is a perspective view of the upper cleat 190 of FIG. 8. The illustrative upper cleat 190 includes a first leg 194b and a second leg 196b, wherein the second leg 196b extends from a distal end of the first leg 194b and in a perpendicular direction to form a channel or receiving slot 198b. A mounting leg 202b may extend from the first leg 194b as shown, for mounting the upper cleat 190 to the first member 124.

FIG. 12 is a perspective view of the second plate or member 126 of the illustrative portable cytometer of FIG. 5. The second member 126 may be fixed to the base 122 by screws that are threaded into screw holes 210a and 210b. As detailed above, the second member 126 may further include a hole 170 that may allow the one or more light sources and one or more light detectors of the optical assembly module 140 to directly access the flow stream window of the removable cartridge.

In the illustrative embodiment, the second member 126 includes a flat major surface with a recessed portion for receiving the removable cartridge. To provide better alignment between the removable cartridge and the first member 124 and/or the second members 126, the second member 126 may include one or more alignment pins 200a–200c that extend toward the first member. The removable cartridge 150 may then include one or more receiving holes for receiving the one or more alignment pins 200a–200c. The alignment pins 200a–200c and receiving holes may provide improved alignment between the removable cartridge and the first member 124 and/or second member 126 when the removable cartridge is secured between the first member 124 and the second member 126.

Additional recesses 212 and 214 may be included to receive the second legs 196a and 196b of the upper L-shaped cleat 190 and lower L-shaped cleat 192, respectively (see FIGS. 8–10). By providing relief for the second legs 196a and 196b of the upper L-shaped cleat 190 and lower L-shaped cleat 192, the removable cartridge may directly engage the surface of the second member 126.

In some cases, the manufacture of the removable cartridge may create a ridge, a burr, or other imperfections, particularly around the outer perimeter of the removable cartridge. In one example, a fluidic cartridge may be manufactured by laminating several layers or sheets together, and then cutting individual fluidic cartridges from the laminated structure. At the cut lines, ridges, burrs, and/or other imperfections may arise. To help the removable cartridge seat flush with the surface of second member 126, a groove 216 or other relief structure may be provided in the receiving surface of the second member 126 to accommodate the one or more imperfections in the removable cartridge. In the illustrative embodiment of FIG. 12, a groove 216 may extend along a groove path that extends around the perimeter of the removable cartridge. It is contemplated, however, that a groove or other relief structure may be provided at any location where an anticipated imperfection might occur in the removable cartridge. It is also contemplated that a groove or other relief structure may be provided in the receiving surface of the first member 124, if desired.

In one illustrative embodiment, the removable cartridge has one or more fluid ports, similar to that described above with respect to FIGS. 1–4. It is contemplated that the one or more fluid ports may be adapted to accept either a gas or a liquid, depending on the application. The second member 126 of the illustrative embodiment includes corresponding fluid ports 220a–220c that align with the one or more fluid ports of the removable cartridge. A fluid port gasket 222 may be secured to the second member 126 to help provide a better seal, if desired.

Having thus described the preferred embodiments of the present invention, those of skill in the art will readily appreciate that the teachings found herein may be applied to yet other embodiments within the scope of the claims hereto attached.

What is claimed is:

1. An apparatus for accepting a removable media member, the removable media member having a front aide, a back aide, and one or more lateral sides extending between the front side and the back side, the apparatus comprising:

a first member;

a second member;

the first member and the second member being adapted to move away from each other along an axis to provide a space for receiving the removable media member, and toward each other along an axis to secure the removable media member; and the first member having a first cleat with a first leg and a second leg, the first leg of the first cleat extending away from the first member and toward the second member, the second leg of the first cleat extending in a lateral direction relative to the first leg, the first leg and the second leg forming a channel for receiving the removable media member such that the first leg engages one or more of the lateral sides of the removable media member the second leg engages at least a portion of the front or the back side of the removable media member.

2. An apparatus according to claim 1 wherein the first leg is positioned so that when the removable media member is received by the first member and the second member, the removable media member is at least roughly aligned with a desired position relative to the first member and/or second member.

3. An apparatus according to claim 2 wherein the second member includes one or more alignment pins, and the removable media member includes one or more receiving holes for receiving the one or more alignment pins.

4. An apparatus according to claim 3 wherein the first leg is positioned so that when the removable media member is received by the first member and the second member, the one or more receiving holes in the removable media member are at least roughly aligned with the one or more alignment pins of the second member.

5. An apparatus according to claim 4 wherein the second leg of the first cleat is adapted to engage the removable media member and pull the removable media from the one or more alignment pins of the second member when the first member and the second member are moved away from each other.

6. An apparatus according to claim 5 wherein the first member further includes a second cleat spaced from the first cleat, the second cleat including a first leg and a second leg, wherein the first leg extends away from the first member and toward the second member, and the second leg extends in a lateral direction relative to the first leg toward the first cleat, the first leg and the second leg of the second cleat forming a channel for receiving the removable media member such that the first leg of the second cleat is positioned adjacent one or more of the lateral sides of the removable media member and the second leg of the second cleat engages at least a portion of one of the front or the back side of the removable media member.

7. An apparatus according to claim 6 wherein the first leg of the first cleat is positioned adjacent one of the lateral sides of the removable media member and the first leg of the second cleat is positioned adjacent an opposing one of the lateral sides of the removable media member.

8. An apparatus according to claim 7 wherein the second leg of the first cleat and the second leg of the second cleat both engage the front side of the removable media member.

9. An apparatus according to claim 8 wherein the removable media member is a fluidic cartridge.

10. An apparatus according to claim 3 wherein at least one of the alignment pins is a stop pin, the stop pin being adapted to engage at least one of the lateral sides of the removable media member when the removable media member is fully inserted between the first member and the second member.

11. An apparatus according to claim 1 wherein the second member is fixed, and the first member is movable toward the second member.

12. An apparatus for accepting a removable media member having one or more electrical contacts, the removable media member having a front side, a back side, and one or more lateral sides extending between the front side and the back side, the apparatus comprising:
   a first member;
   a second member;
   the first member and the second member being adapted to move away from each other to provide a space for receiving the removable media member, and toward each other to secure the removable media member; and
   the first member having one or more spring biased probes extending outward toward the second member, the one or more spring biased probes being positioned to align with at least selected ones of the one or more electrical contacts of the removable media member when the removable media member is at a desired positioned between the first member and the second member.

13. An apparatus according to claim 12 wherein at least one of the first member and second member includes one or more alignment pins, and the removable media member includes one or more receiving holes for receiving the one or more alignment pins when the removable media member is at the desired position between the first member and the second member.

14. An apparatus according to claim 12 wherein the first member further includes outward bias means for providing a bias force to the removable media member, the bias force being directed away from the first member.

15. An apparatus according to claim 14 wherein the bias force of the outward bias means is overcome when the first member and the second member are moved toward each other to secure the removable media member.

16. An apparatus according to claim 15 wherein the bias force of the outward bias means pushes the removable media member away from the one or more spring biased probes when the first member and the second member are moved away from each other.

17. An apparatus according to claim 14 wherein the outward bias means includes a spring.

18. An apparatus according to claim 17 wherein the outward bias means includes a wedge that is biased to an outward position away from the first member by the spring.

19. An apparatus according to claim 12 wherein the removable media member is a fluidic cartridge.

20. An apparatus according to claim 19 wherein the removable media member includes:
   one or more flow channels; and
   one or more flow sensors in fluid communication with selected ones of the one or more of the flow channels, the one or more flow sensors being electrically connected to selected ones of the one or more electrical contacts.

21. An apparatus according to claim 19 wherein the removable media member includes one or more pumps, wherein the one or more pumps are electrically connected to selected ones of the one or more electrical contacts.

22. An apparatus comprising:
   a removable media member including one or more sensors and/or actuatable devices, the removable media member further including communication means wherein at least one of the one or more sensors and/or actuatable devices is in communication with the communication means of the removable media member; and
   a base adapted to receive the removable media member, the base including communication means that is adapted to communicate with the communication means of the removable media member.

23. An apparatus according to claim 22 wherein the removable media member includes one or more detectors and the base includes one or more emitters.

24. An apparatus according to claim 23 wherein the one or more detectors of the removable media member include one or more optical detectors, and the one or more emitters of the base includes one or more optical emitters.

25. An apparatus according to claim 23 wherein the one or more detector of the removable media member include one or more RF detectors, and the one or more emitters of the base includes one or more RF emitters.

26. An apparatus according to claim 22 wherein the removable media member includes one or more emitters and the base includes one or more detectors.

27. An apparatus according to claim 26 wherein the one or more emitters of the removable media member include one or more optical emitters, and the one or more detectors of the base includes one or more optical detectors.

28. An apparatus according to claim 27 wherein the one or more emitters of the removable media member include one or more RP emitters, and the one or more detectors of the base includes one or more RF detectors.

29. An apparatus for accepting a removable media member that has one or more fluid ports, the removable media member having a front side, a back side, and one or more lateral sides extending between the front side and the back side, the apparatus comprising:

a first member;

a second member;

the first member and the second member being adapted to move away from each other to provide a space for receiving the removable media member, and toward each other to secure the removable media member; and the first member having one or more fluid polls, the one or more fluid ports being positioned to align with at least selected ones of the fluid ports of the removable media member when the removable media member is secured by the first member and the second member.

30. An apparatus according to claim 29 wherein one or both of the first member and the second member include one or more alignment pins, and the removable media member includes one or more holes for accepting the one or more alignment pins.

31. An apparatus according to claim 29 wherein a seal is formed between the one or more fluid ports of the first member and the one or more fluid ports of the removable media member when the first member and the second member are moved toward each other to secure the removable media member.

32. An apparatus according to claim 29 further including means for moving the removable media member away from the one or more fluid ports of the first member when the first member and the second member are moved away from each other.

33. An apparatus according to claim 29 wherein the one or more fluid ports of the first member and the one or more fluid ports of the removable media member are adapted to transport a gas.

34. An apparatus according to claim 29 wherein the one or more fluid ports of the first member and the one or more fluid ports of the removable media member are adapted to transport a liquid.

35. An apparatus according to claim 29 wherein the removable media member is a fluidic cartridge.

36. An apparatus for accepting a removable media member that has one or more electrical contacts and one or more fluid ports, the removable media member having a front side, a back side, and one or more lateral sides extending between the front side and the back side, the apparatus comprising:

a first member;

a second member;

the first member and the second member being adapted to move away from each other to provide a space for receiving the removable media member, and toward each other to secure the removable media member; and at least one of the first member and/or second member having one or more spring biased probe, the one or more spring biased probe being positioned to align with at least selected ones of the one or more electrical contacts on the removable media member when the removable media member is received by the first member and the second member; and at least one of the first member and/or second member having one or more fluid ports, the one or more fluid ports being positioned to align with at least selected ones of the fluid ports of the removable media member when the removable media member is received by the first member and the second member.

37. An apparatus according to claim 36 wherein at least one of the first member and/or second member farther includes outward bias means for providing a bias force to the removable media member away from the one or more spring biased probes.

38. An apparatus according to claim 36 wherein a seal is formed between the one or more fluid ports of the at least one of the first member and/or second member and the one or more fluid ports of the removable media member when the first member and the second member are moved toward each other to secure the removable media member.

39. An apparatus for accepting a removable media member, the removable media member having a front side, a back side, and one or more lateral sides extending between the front side and the back side, the apparatus comprising:

a first member;

a second member;

the first member and the second member being adapted to move away from each other to provide a space for receiving the removable media member, and toward each other to secure the removable media member; and the first member having a groove therein, the groove extending along a groove path that corresponds to the perimeter of the front side of the removable media member when the removable media member is at a desired position relative to the first member and the second member.

40. An apparatus according to claim 39 wherein the removable media member includes a number of imperfections around the perimeter of the front side of the removable media member, and the groove provides relief apace for the number of imperfections.

41. An apparatus according to claim 39 wherein the removable media member is a fluidic cartridge.

42. A method for accepting a removable media member, the removable media member having a front side, a back side, and one or more lateral sides extending between the front side and the back side, the method comprising the steps of:

providing a first member;

providing a second member;

moving the first member and the second member away from each other along an axis to provide a space therebetween;

inserting the removable media member into the space between the first member and the second member;

moving the first member and the second member toward each other along an axis to secure the removable media member;

moving the first member and the second member away from each other along an axis; and moving the removable media member with the first member when the first member and the second member are moved away from each other.

43. A method according to claim 42 wherein the second member includes one or more alignment pins, and the removable media member includes one or more receiving holes for receiving the one or more alignment pins, the one or more receiving holes of the removable media member receiving the one or more alignment pins when the first member and the second member are moved toward each other to secure the removable media member.

44. A method according to claim 43 wherein the one or more alignment pins are removed from the one or more boles of the removable media member when the removable media member is moved with the first member when the first member and the second member are moved away from each other.

45. A method according to claim 43 wherein the removable media member is a fluidic cartridge.

46. A method for accepting a removable media member, having one or more electrical contacts, the removable media member having a front side, a back side, and one or more lateral sides extending between the front side and the back side, the method comprising the steps of:
 providing a first member and a second member, the first member having one or more spring biased probes extending outward toward the second member, the one or more spring biased probes being positioned to align with at least selected ones of the one or more electrical contacts of the removable media member when the removable media member is received by the first member and the second member;
 moving the first member and the second member away from each other to provide a space therebetween;
 inserting the removable media member into the space between the first member and the second member; and
 moving the first member and the second member toward each other to receive the removable media member such that at least selected ones of the one or more spring biased probes make electrical contact with one or more of the electrical contacts of the removable media member.

47. A method according to claim 46 further comprising the steps of:
 moving the first member and the second member away from each other; and
 moving the removable media member away from the first member when the first member and the second member are moved away from each other.

48. A method according to claim 46 wherein the removable media member is a fluidic cartridge.

49. A method according to claim 48 wherein the removable media member includes:
 one or more flow channels; and
 one or more flow sensors in fluid communication with selected ones of the one or more of the flow channels, the one or more flow sensors being electrically connected to selected ones of the one or more electrical contacts.

50. A method according to claim 46 wherein the removable media member includes one or more detectors, wherein the one or more detectors are electrically connected to selected ones of the one or more electrical contacts.

51. A method according to claim 50 wherein the one or more detectors include one or more optical detectors.

52. A method according to claim 46 wherein the removable media member includes one or more optical emitter., wherein the one or more optical emitters are electrically connected to selected ones of the one or more electrical contacts.

53. A method according to claim 46 wherein the removable media member includes one or more pumps, wherein the one or more pumps are electrically connected to selected ones of the one or more electrical contacts.

54. An apparatus comprising:
 a removable media member including one or more pneumatically responsive elements; and
 a base adapted to receive the removable media member, the base including one or more pneumatic sources,
 wherein when the removable media member is received by the base, at least one of the pneumatic sources of the base are in fluid communication with at least one of the pneumatically responsive elements of the removable media member.

55. An apparatus according to claim 54 wherein the one or more pneumatically responsive elements includes a pneumatically actuated valve.

56. An apparatus according to claim 54 wherein the one or more pneumatically responsive elements includes an element that produces pneumatically controlled mechanical movement.

57. An apparatus according to claim 56 wherein the element that produces pneumatically controlled mechanical movement is a pneumatically controlled pump.

58. An apparatus for accepting a removable media member, the removable media member having an interface that is adapted to interface with a corresponding interface of the apparatus, the apparatus comprising:
 a receiver slot for receiving the removable media member, the interface of the apparatus being positioned to align with the interface of the removable media member when the removable media member is inserted to a predetermined position in the receiver slot; and
 bias means extending into the receiver slot for biasing the interface of the removable media member away from the interface of the apparatus when the removable media member is being inserted into the receiver slot.

59. The apparatus of claim 58 further comprising:
 a movable member that is selectively moveable in a first direction to push the removable media member, working against the bias means, until the interface of the removable media member engages the interface of the apparatus after the removable media member is inserted to the predetermined position in the receiver slot.

60. The apparatus of claim 59 wherein the movable member is selectively moveable in a second direction, which allows the biasing means to help move the interface of the removable media member away from the interface of the apparatus.

61. The apparatus of claim 58 wherein the receiver slot is at least partially defined by one or more L-shaped cleats.

62. The apparatus of claim 58 wherein the interface of the removable member includes a number of contacts.

63. The apparatus of claim 58 wherein the interface of the apparatus includes a number of contacts.

64. The apparatus of claim 63 wherein the number of contacts of the interface of the apparatus include a number of spring bias probes.

65. The apparatus of claim 58 wherein the bias means includes a spring.

66. The apparatus of claim 65 wherein the bias means includes a wedge biased by the spring, wherein the wedge is biased into the receiver slot for biasing the interface of the removable media member away from the interface of the apparatus when the removable media member is inserted into the receiver slot.

67. The apparatus of claim 66 wherein the wedge has a chamfer that helps provide easier insertion of the removable media member into the receiver slot.

68. A method for loading and unloading a removable media member having one or more electrical contacts, the removable media member having a front side, a back side, and one or more lateral sides extending between the front side and the back side, the method comprising the steps of:
 providing a body including a first member and a second member, wherein the body has one or more contacts that align with the one or more electrical contacts of the removable media member when the removable media member is inserted at a predetermined position between the first member and the second member;
 biasing the removable media member away from the first member such that the one or more contacts of the body do not engage the one or more electrical contacts of the removable media member;

moving the first member and the second member toward each other, overcoming the bias, such that at least selected ones of the one or more contacts of the body engage and make electrical contact with one or more contacts of the removable media member; and moving the first member sad the second member away from each other, the biasing step helping to push the removable media member away from the first member, thereby breaking the electrical contact between the one or more contacts of the removable media member and the one or more contacts of the body.

69. The method of claim 68 wherein the bias step is performed using a spring.

70. Tho method of claim 69 wherein the biasing step is performed using a wedge that is biased with the spring.

71. The method of claim 70 wherein the wedge has a chamfer.

* * * * *